United States Patent [19]

Kaufman

[11] Patent Number: 4,740,461

[45] Date of Patent: Apr. 26, 1988

[54] VECTORS AND METHODS FOR TRANSFORMATION OF EUCARYOTIC CELLS

[75] Inventor: Randal J. Kaufman, Boston, Mass.

[73] Assignee: Genetics Institute, Inc., Cambridge, Mass.

[21] Appl. No.: 566,057

[22] Filed: Dec. 27, 1983

[51] Int. Cl.$^4$ .................. C12P 21/00; C12P 21/02; C12N 15/00; C12N 05/00

[52] U.S. Cl. .................. 435/68; 435/172.3; 435/70; 435/240.2; 935/32; 935/56; 935/33; 935/70

[58] Field of Search .................. 435/68, 172.3, 240, 435/948; 935/32, 33, 36, 56, 70, 71

[56] References Cited

U.S. PATENT DOCUMENTS

| | | | |
|---|---|---|---|
| 4,318,690 | 5/1985 | Guntaka | 435/253 |
| 4,399,216 | 8/1983 | Axel et al. | 435/948 |
| 4,510,245 | 4/1985 | Cousens et al. | 435/68 |
| 4,511,652 | 4/1985 | Fogel et al. | 435/68 |

OTHER PUBLICATIONS

Feldman et al. "Activation of Early Adenovirus Transcription by Herpesvirus Immediate Early Gene: Evidence for a Common Factor", *Proceedings of the National Academy of Sciences* 79 pp. 4952–4956 (1982).

Mercola et al., "Transcriptional Enhancer Elements in the Mouse Immunoglobulin Heavy Chain Locus" Science 221 pp. 663–665 (1983).

Banerji et al., "A Lymphocyte-Specific Cellular Enhancer is Located Downstream of the Joining Region in Immunoglobulin Genes" Cell 33 pp. 729–740 (1983).

Gillies et al., "A Tissue Specific Transcription Enhancer Element is Located in the Major Intron of a Rearranged Gene" Cell 33 pp. 717–728 (1983).

Banerji et al., "Expression of a Beta-Globin Gene is Enhanced by Remote SV40 DNA Sequences" Cell 27 pp. 299–308 (1982).

deVilliers et al., "A Small Segment of Polyoma Virus DNA Enhances the Expression of a Cloned Beta--Globin Gene" Nucleic Acids Research 9(23) pp. 6251–6265 (1981).

Moreau et al., "The SV40 72 Base Pair Repeat has a Striking Effect on Gene Expression Both in SV40 and Other Chimeric" Nucleic Acids Research 9(22) pp. 6047–6068 (1981).

Laimins et al., "Host-Specific Activation of Transcription by Tandem Repeats from Simian Virus 40 and Molony Murino Sarcoma" Proceedings of the National Academy of Sciences 79 pp. 6453–6457 (1982).

Kaufman et al., "Construction of a Modular Dihydrofolate Reductase cDNA Gene Analysis of Signals Utilized for Efficient Expression" Molecular and Cellular Biology 2 pp. 1304–1319 (1982).

*Primary Examiner*—John Edward Tarcza
*Attorney, Agent, or Firm*—David L. Berstein; Bruce M. Eisen; Mary E. Bak

[57] ABSTRACT

Eucaryotic cells cotransformed with product and selection genes yield considerably greater quantities of product after a novel subcloning strategy is employed: Transformants are identified for product yield, cultured under selection pressure and the progeny screened for product yield. Novel transformation vectors contain directly ligated selection and product genes and/or eucaryotic promoters.

12 Claims, 12 Drawing Sheets

| | | | | | | | | | | | | | | | | | | | |
|---|---|---|---|---|---|---|---|---|---|---|---|---|---|---|---|---|---|---|---|
| Tyr TAC | Phe TTT | Gly GGG | Asn AAT | Ser TCA | Gly GGG | Ala GCC | Tyr TAC | Arg CGT | Gly GGC | Thr ACC | His CAC | Ser AGC | Leu CTC | Thr ACC | Glu GAG | Ser TCG | Gly GGT | Ala GCC | Ser TCC |
| Cys TGC | Leu CTC | Pro CCC | Trp TGG | Ser TCC | Asn AAT | MET ATG | Ile ATC | Leu CTG | Ile ATA | Gly GGC | Lys AAG | Val GTT | Tyr TAC | Thr ACA | Ala GCA | Gln CAG | Asn AAC | Pro CCC | Ser AGT |
| Ala GCC | Gln CAG | Ala GCA | Leu CTC | Leu CTC | Gly GGC | Gly GGC | Lys AAG | His CAT | Lys AAA | Tyr TAC | Cys TGC | Arg CGG | Asn AAT | Pro CCT | Asp GAT | Gly GGG | Asp GAT | Ala GCC | Lys AAG |
| Pro CCC | Trp TGG | Cys TGC | His CAC | MET ATG | Gly GGC | Lys AAG | Asn AAC | Arg CGC | Arg AGG | Leu CTG | Thr ACG | Trp TGG | Glu GAG | Tyr TAC | Cys TGT | Asp GAT | Val GTC | Val GTC | Ser TCC |
| Cys TGC | Ser TCC | Thr ACC | Cys TGC | Gly GGC | Leu CTG | Arg AGA | Tyr TAC | Trp TGG | Ser AGC | Gln CAG | Pro CCT | Gln CAG | Phe TTT | Arg CGC | Ile ATC | Lys AAA | Gly GGA | Gly GGG | Leu CTC |
| Phe TTC | Ala GCC | Asp GAC | Ile ATC | Ala GCC | Phe TTC | His CAC | Trp TGG | Pro CCG | Gln CAG | Ala GCT | Ala GCC | Ile ATC | Phe TTT | Ala GCC | Ile ATC | His CAC | Arg AGG | Arg AGG | Ser TCG |
| Pro CCC | Gly GGA | Glu GAG | Arg CGG | Phe TTC | Gln CAG | Pro CCT | Gly GGG | Pro CCG | Ile ATA | Leu CTC | Ile ATC | Ser AGC | Ser TCC | Cys TGC | Lys AAG | Ile ATT | Leu CTC | Ser TCT | Ala GCC |
| Ala GCC | His CAC | Cys TGC | Phe TTC | Gln CAG | Glu GAG | Pro CCC | Gln CAG | Gln CAG | Pro CCC | His CAC | Lys AAA | Leu CTG | Thr ACG | Val GTG | Glu GAA | Ile ATC | Leu CTG | Gly GGC | Thr ACA |
| Tyr TAC | Arg CGG | Val GTC | Asp GAT | Pro CCT | Asp GAT | Asp GAT | Thr ACT | Tyr TAC | Gln CAG | Lys AAA | Phe TTT | Glu GAA | Val GTC | Glu GAA | Lys AAA | Lys AAA | Tyr TAC | Ile ATT | His CAT |
| Lys AAG | Glu GAA | Phe TTC | Asp GAT | Asp GAC | Asp GAT | Glu GAG | Thr ACT | Tyr TAC | Asn AAT | Asp GAC | Ala GCG | Ala GCC | Leu CTG | Lys AAA | Gln CAG | Leu CTG | Lys AAA | Ser TCG | Asp GAT |
| Ser TCG | Arg CGC | Ser TCC | Cys TGT | Ala GCC | Gln CAG | Glu GAG | Ser AGC | Val GTG | Ser AGC | Val GTC | Thr ACT | Val GTG | Val GTG | Cys TGC | Pro CCC | Leu CTT | Pro CCC | Ala GCG | Asp GAC |

FIG 1C

| Leu CTG | Gln CAG | Leu CTG | Pro CCG | Asp GAC | Trp TGG | Thr ACG | Glu GAG | Cys TGT | Leu CTC | Ser TCC | Gly GGC | Tyr TAC | Gly GGC | Lys AAG | His CAT | Glu GAG | Ala GCC | Leu TTG |
| Ser TCT | Pro CCT | Phe TTC | Tyr TAT | Ser TCG | Glu GAG | Arg CGG | Leu CTG | Lys AAG | Ala GCT | His CAT | Val GTC | Arg AGA | Leu CTG | Tyr TAC | Pro CCA | Ser TCC | Ser AGC | Arg CGC |
| Cys TGC | Thr ACA | Ser TCA | Gln CAA | His CAT | Leu TTA | Leu CTT | Asn AAC | | Val GTC | Thr ACC | Asp GAC | Asn AAC | MET ATG | Leu CTG | Pro CCA | Ala GCT | Gly GGA | Asp GAC |
| Thr ACT | Arg CGG | Ser AGC | Gly GGC | Gly GGG | Pro CCC | Gln CAG | Ala GCA | Arg CGC | His CAC | Asp GAC | Ala GCC | Cys TGC | Gln CAG | Gly GGC | Cys TGT | Asp GAT | Ser TCC | Gly GGA |
| Pro CCC | Leu CTG | Val GTG | Cys TGT | Leu CTC | Asn AAC | Asp GAT | Gly GGC | Arg CGC | Thr ACT | Leu TTG | Leu TTG | Gly GGC | Ile ATC | Ile ATC | Ser AGC | Trp TGG | Gly GGG | Leu CTG |
| Gly GGC | Cys TGT | Gln CAG | Gln CAG | Lys AAG | Asp GAT | Val GTC | Pro CCG | Gly GGT | MET ATG | Thr ACT | Thr ACC | Ile ATC | Thr ACC | Thr ACC | Trp TGG | Leu CTA | Asp GAC | Trp TGG |
| Ile ATT | Arg CGT | Asp GAC | Asn AAC | MET ATG | Arg CGA | Pro CCG | TGA | | Tyr TAC | Tyr TAC | Lys AAG | Val GTT | | Asn AAC | Tyr TAC | | | |

CTGCAAAGGCGCAGTGCTTCTCTACAGACTTCTCCAGACTCCTCAAAAGCAAATGAGATCCCCCGCTCTTCTTCAGAAGACA
TACTTCCCATTTGGAAGTTTCAGGACTTGTCTCATTTCAGGACCTCAGAAGGCGGACGAGACCCTACAGGAGAGGAAGAGTGCATTTCCCAGA
TCCCTGGGCAGAAAGTGCCATGGACTTCAGCTAAAGCCAACCTCCTGTCACCCGTGACCTTTGGAAACAGGACCACAAAAATGA
AAGCATGTCTCAATAGTAAAGATAACAAGATCTTTCAGGAAAGACGGATTGCATTAGAAATAGACAGTATATTTATAGTCACAAGAGCCAGCCG
GCTCAAAGTTGGGCAGGCTGGCTGGGTCATGTCCAAAAGACCCTTGACGTCAAGTCTCCCTTCCCCACTCCCTGGCTCTCAGAAGGTAT
TCCTTTTGTGTACAGTGTGTAAAGTGTAATCCTTTTCTTTATAAACTTTAGAGTAGCATGAGAGAATTGTATCATTGAACAACTAGGCTTCAGCATAT
TTATAGCAATCCATGTTAGTTTTACTTTCTGTTGCCACACCCTGTTTTATACTGTACTAATAAATTCAGATATATTTTCACAGTTTTCCAAAAAA
AAAAAAA1

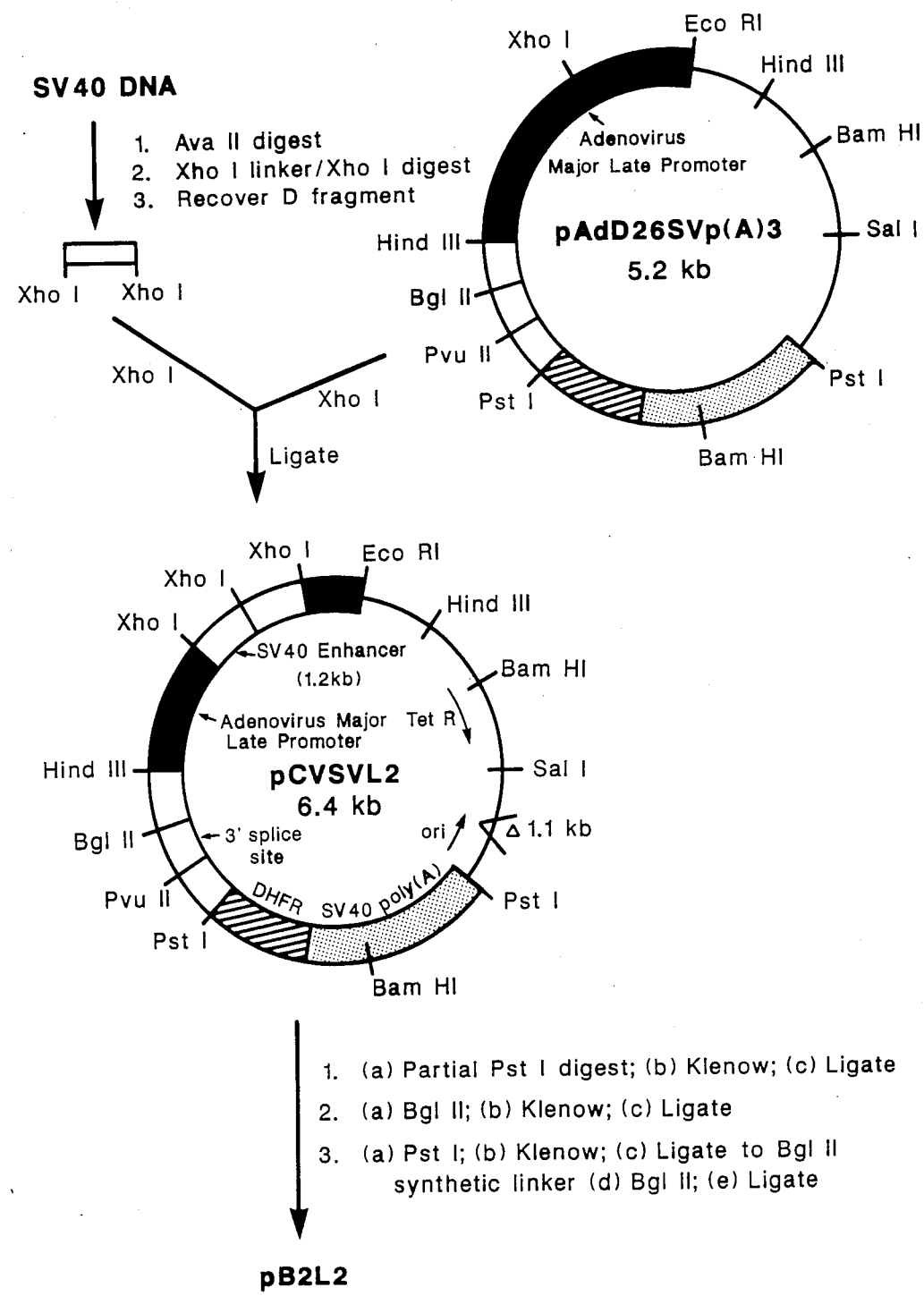

VECTORS AND METHODS FOR TRANSFORMATION OF EUCARYOTIC CELLS

BACKGROUND

This invention relates to the production of proteins of interest by eucaryotic cells transformed with selectable markers. In particular, it is concerned with obtaining high yields of secreted, commercially useful proteins such as tissue plasminogen activator from cultured eucaryotic cells which have been cotransformed with genes coding for the protein and for a selectable marker.

The following definitions are supplied in order to facilitate the understanding of this case. To the extent that the definitions vary from meanings circulating within the art, the definitions below are to control.

Amplification means the process by which cells produce gene repeats within their chromosomal DNA.

Cotransformation means the process of transforming a cell with more than one exogenous gene foreign to the cell, one of which confers a selectable phenotype on the cell.

Downstream means the direction going towards the 3' end of a nucleotide sequence.

An enhancer is a nucleotide sequence that can potentiate the transcription of genes independent of the identity of the gene, the position of the sequence in relation to the gene, or the orientation of the sequence.

A gene is a deoxyribonucleotide sequence coding for a given mature protein. For the purposes herein, a gene shall not include untranslated flanking regions such as RNA transcription initiation signals, polyadenylation addition sites, promoters or enhancers.

A selection gene is a gene that confers a phenotype on cells which express the gene as a detectable protein.

A selection agent is a condition or substance that enables one to detect the expression of a selection gene.

Phenotype means the observable properties of a cell as expressed by the cellular genotype.

A product gene is a gene that encodes a protein product having desirable characteristics such as diagnostic or therapeutic utility.

Genotype means the genetic information contained within a cell as opposed to its expression, which is observed as the phenotype.

Ligation is the process for forming a phosphodiester bond between the 5' and 3' ends of two DNA strands. This may be accomplished by several well known enzymatic techniques, including blunt end ligation by T4 DNA ligase.

Orientation refers to the order of nucleotides in a DNA sequence. An inverted orientation of a DNA sequence is one in which the 5' to 3' order of the sequence in relation to another sequence is reversed when compared to a point of reference in the DNA from which the sequence was obtained. Such points of reference can include the direction of transcription of other specified DNA sequences in the source DNA or the origin of replication of replicable vectors containing the sequence.

Transcription means the synthesis of RNA from a DNA template.

Transformation means changing a cell's genotype by the cellular uptake of exogenous DNA. Transformation may be detected in some cases by an alteration in cell phenotype. Transformed cells are called transformants. Pre-transformation cells are referred to as parental cells.

Translation means the synthesis of a polypeptide from messenger RNA.

The transformation of higher, i.e. non-fungal, eucaryotic cells with genes capable of conferring selectable phenotypes has received increasing interest as a method for detecting transformed cells containing amplified genes responsible for selectable phenotypes.

Eucaryotic transformation is in general a well-known process, and may be accomplished by a variety of standard methods. These include the use of protoplast fusion, DNA microinjection, chromosome transfection, lytic and nonlytic viral vectors (For example, Mulligan et al., "Nature"(London) 277:108-114 [1979], cell-cell fusion (Fournier et al., "Proc. Nat. Acad. Sci."74:3-19-323 [1977], lipid structures (U.S. Pat. No. 4,394,448) and cellular endocytosis of DNA precipitates (Bachetti et al., "Proc. Nat. Acad. Sci. 74:1590-1594 [1977].

Transformation which is mediated by lytic viral vectors is efficient but is disadvantageous for a number of reasons: The maximum size of transfected DNA is limited by the geometry of viral capsid packing, the exogenous genes which are frequently deleted during viral replication, and the requirement for helper virus or specialized hosts, also host cells must be permissive, and the hosts are killed in the course of viral infection.

Some nonlytic viral transformations are based on the transcription and translation of virus vectors which have been incorporated into a cell line as a stable episome. These systems generally require unique cell lines and suffer from a number of disadvantages. See "Trends in Biochemical Sciences", June 1983, pp. 209-212.

On the other hand, other transformations in which extrachromosomal DNA is taken up into the chromosomes of host cells have been characterized by low frequencies of transformation and poor expression levels. These initial difficulties were ameliorated by transformation with genes which inheritably confer selectable phenotypes on the small subpopulation of cells that are in fact transformed. The entire population of transformed cells can be grown under conditions favoring cells having acquired the phenotype, thus making it possible to locate transformed cells conveniently. Thereafter, transformants can be screened for the capability to more intensely express the phenotype. This is accomplished by changing a selection agent in such a way as to detect higher expression.

Selection genes fall into three categories: detectably amplified selection genes, dominant selection genes, and detectably amplified dominant selection genes.

Detectably amplified selection genes are those in which amplification can be detected by exposing host cells to changes in the selection agent. Detectably amplified genes which are not dominant acting generally require a parental cell line which is genotypically deficient in the selection gene. Examples include the genes for asparagine synthetase; aspartate transcarbamylase; (Kemp et al., "Cell"9:541 [1976], adenylate deaminase (DeBatisse et al., "Mol and Cell Biol."2(11):1346-1353 [1982] mouse dihydrofolate reductase (DHFR) and, with a defective promoter, mouse thymidine kinase (TK).

Dominant selection genes are those which are expressed in transformants regardless of the genotype of the parental cell. Most dominant selection genes are not detectably amplified because the phenotype is so highly effective in dealing with the selection agent that it is difficult to discriminate among cell lines that have or have not amplified the gene. Examples of dominant selection genes of this type include the genes for procaryotic enzymes such as xanthine-guanine phosphoriboxyltransferase (Mulligan et al., "Proc. Nat. Acad. Sci."78[4]:2072-2076 [1981] and aminoglycoside 3—phosphotransferase (Colbere-Garapin et al., "J. Mol. Biol.", 150:1-14 [1981].

Some dominant selection genes also are detectably amplified. Suitable examples include the mutant DHFR gene described by Haber et al., "Somatic Cell Genet."4:499-508 [1982], cell surface markers such as HLA antigens and genes coding for enzymes such as specific esterases that produce fluorescent or colored products from fluorogenic or chromogenic substrates as is known in the art.

Detectably-amplified, dominant selection genes are preferred for use herein. It should be understood that a dominant selection gene in some cases can be converted to a detectably amplified gene by suitable mutations in the gene.

Selection genes at first were of limited commercial utility. While they enabled one to select transformants having the propensity to amplify uptaken DNA, most selection genes produced products of no commercial value. On the other hand, genes for products which were commercially valuable generally did not confer readily selectable (or even detectable) phenotypes on their transformants. This would be the case, for example, with enzymes or hormones which do not provide transformed cells with unique nutrient metabolic or detoxification capabilities. Most proteins of commercial interest fall into this group, e.g. hormones, proteins participating in blood coagulation and fibrinolytic enzymes.

Subsequently it was found that eucaryotic cells having the propensity to be transformed with and amplify the selection gene would do the same in the case of the product gene. By following the selection gene one could identify a subpopulation of transformant cells which coexpress and coamplify the product gene along with the selection gene. It has been the practice to culture the transformants in the presence of the selection agent and to conclude that transformants having increased expression of the selection gene will also show increased expression of the product gene. Axel et al., U.S. Pat. No. 4,399,216 use the term cotransformation to describe the process of transforming a cell with more than one different gene, whether by vector systems containing covalently linked or unlinked genes, and in the latter case whether the genes are introduced into host cells sequentially or simultaneously. Cotransformation should "allow the introduction and stable integration of virtually any defined gene into cultured cells"-(Wigler et al., "Cell", 16:777-785, [1979], and "by use of the cotransformation process it is possible to produce eucaryotic cells which synthesize desired proteinaceous and other materials"(U.S. Pat. No. 4,399,216, column 3, lines 37-42.)

SUMMARY OF THE INVENTION

The present invention comprises a method for expressing heterologous protein in eucaryotic cells that is capable of increasing the yield of such protein many fold. In accord with the present invention, a method is provided for subcloning a eucaryotic cell that has been transformed to express a selectable phenotype and a product and that has been cultured to a cell population under conditions desiqned to select for expression of the phenotype, said method comprising (a) selecting one or more cells from the parent cell population that express the product in a preferential fashion when compared to other cells in the parent population, (b) culturing the selected cell or cells to a subsequent cell population under conditions designed to select for a change in the expression of the phenotype, and (c) further selecting one or more cells from the subsequent cell population that express the product in a preferential fashion when compared to other cells in the subsequent cell population.

Transformation Vectors

Vectors used in cotransformation will contain a selection gene and/or a product gene. In addition there usually will be present in transformation or cotransformation vectors other elements such as enhancers, promoters, introns, accessory DNA, polyadenylation sites and 3' noncoding regions as will be described below.

Suitable selection genes are described above. It is preferred that the selection agent be one that prevents cell growth in the absence of the selection gene. That way, revertant cells in long term culture that delete or no longer express the selection gene (and presumably the product gene as well) will not over-grow the population. However, it would be desirable in the commercial production of product proteins for therapeutic purposes to avoid the use of cell toxins, thereby simplifying the product purification steps. Thus, a desirable selection gene would be one that enables transformants to use a nutrient critical for growth that they otherwise would not be able to use. The TK gene described above is an example. It should also be kept in mind that a selection gene also may be the product gene. For example, one might wish to harvest the products of selection genes for use as therapeutic or diagnostic agents.

The product genes which can be used are essentially unlimited. Genes coding for substances that are proteins or that can be made by protein-based reactions such as enzyme conversions are suitable. Genes for proteins that may adversely affect the host cells by synthesizing toxins or hydrolyzing host proteins, e.g. some enzymes from procaryotic or lower eucaryotic sources, may be employed with qualifications such as providing antitoxins in the culture medium or by selecting for lower expression levels that would otherwise be optimum. Genes for proteins or enzymes having activities that are found in the cells of higher animals such as mammals or vertebrates are also suitable. The genes of interest for most therapeutic proteins will be of this class.

Product genes can become capable of functioning as selection genes if the environment of the transformant can be modified to enable the product to give the transformants some selection advantage. For example, a product gene can produce an enzyme which will act upon an otherwise unusable critical substrate in the cell medium to release the critical substrate, e.g. an obligatory nutrient.

Exemplary product genes are genes coding for blood clotting or fibrinolysis proteins such as antihemophilic factor, tissue plasminogen activator, urokinase and clotting factors II, VII, IX, X or XIII, blood proteins such as fibronectin or albumin, hormones or regulatory proteins including lymphokines and other T-cell active substances, growth hormones and platelet derived growth factor, oncogene products, cell surface antigens, immune proteins such as IgG, IgE and IgM as well as complement, and other proteins that are or become of commerical interest.

Two classes of vectors have been employed in cotransformation. The first class are the unlinked vectors. Here the selection gene and the product gene are not covalently bound. This vector class is preferred because the step of ligating or otherwise bonding the two genes is not required. This simplifies the transformation process because the selection and product genes usually are obtained from separate sources and are not ligated in their wild-type environment. In addition, the molar ratio of the product and selection genes employed during cotransformation can be adjusted to increase cotransformation efficiency.

The second class of cotransformation vectors are linked vectors. These vectors are distinguished from unlinked vectors in that the selection and product genes are covalently bound, preferably by ligation.

The selection and product genes employed herein may be accompanied by all or a portion of their wild type, untranslated flanking sequences, but ordinarily such sequences will not be included as is further described below. In the case of a linked vector particularly beneficial results in product yield are obtained by positioning the product gene upstream from and linked closely to the translated regions of the selection gene. This generally means that most if not all of the 3' untranslated region found downstream from the wild-type product gene and the 5' untranslated regions found upstream from the wild-type selection gene are excised by appropriate restriction endonucleases, or by deletion via oligonucleotide priming with M13 as disclosed elsewhere herein. The result is that both genes are directly ligated without the insertion of a promoter between the product and selection gene.

The genes described herein will ordinarily contain the wild-type translated sequences encoding prepro polypeptides, e.g. secretory leaders, which may be desirable for the structure, stability and/or secretion of the mature product. However, if translated wild-type leader sequences do not function properly within the transformants, then such prepro sequences can be deleted prior to assembly into a vector and cotransformation of the host cell.

It ordinarily is not material that the vectors or the genes contained within the vectors are interrupted with introns so long as the messenger RNA transcripts from the vectors are spliced properly by the transformants to yield messenger RNA which is translated into the mature protein, plus any desired leader sequences. This will be the case among introns found in the genes of a given higher eucaryotic cell which are to be processed by other higher eucaryotic cells. Since most genes used herein are cDNA reverse transcripts no introns will be present, and the possibility of erroneous post-transcriptional splicing will be reduced considerably.

In the case of linked vectors, the coding strands for the selection and product genes are preferably joined by directly ligating the product stop codon to the selection gene start codon. Alternatively, the genes are ligated through an oligodeoxyribonucleotide bridge which is rich in the guanine and cytosine deoxyribonucleotides (G and C, respectively). The bridge should be free of termination and start codons, and palindromes so as to reduce the probability of forming RNA hairpin loops.

The terms "product gene" and "selection gene" are not intended to imply that only one of each gene or a single copy of each gene is intended for use in the vectors. First, a given selection phenotype may require the synthesis of more than one discrete protein. In this case, for example, the selection gene for each protein could be present in a vector which is covalently unlinked to either the product gene or any other selection gene, or each selection gene could be ligated to the product gene as described above or in U.S. Pat. No. 4,399,216. It is not preferred to use more than one selection gene where each gene would confer a selection phenotype for the same selection agent independently of any other selection gene.

It may be desirable to transform with a vector or vectors containing a plurality of discrete product genes. Discrete product genes which encode proteins having a beneficial effect on one another are particularly interesting. For example, one can coexpress a protein that stabilizes another product protein or which is part of a multiple protein system in its biologically active mode.

In addition, either or both of the selection and product genes may be repeated in the vector or vectors, i.e., present in multiple, generally tandem, copies. In such cases each of the repeated genes preferably will contain all of the RNA processing and transcriptional control sequences present in vectors containing only a single copy of the genes.

The vectors herein may also include enhancers. Enhancers are functionally distinct from promoters, but appear to operate in concert with promoters. Their function on the cellular level is not well understood, but their unique characteristic is the ability to activate or potentiate transcription without being position or orientation dependent. Promoters need to be upstream of the gene, while enhancers may be present upstream or 5' from the promoter, within the gene as the intron, or downstream from the gene between the gene and a polyadenylation site or 3' from the polyadenylation site. Inverted promoters are not functional, but inverted enhancers are. Enhancers are cis-acting, i.e., they have an effect on promoters only if they are present on the same DNA molecule. For a general discussion of enhancers see Khoury et al., "Cell"33:313-314 [1983].

Preferred enhancers are obtained from animal viruses such as simian virus 40, polyoma virus, bovine papilloma virus, retrovirus or adenovirus. Ideally, the enhancer should be from a virus for which the host cell is permissive, i.e. which normally infects cells of the host type. Viral enhancers can be obtained readily from publically available viruses. The enhancer regions for several viruses, e.g., Rous sarcoma virus and simian virus 40, are well known. See Luciew et al., "Cell"33:7-05-716 (1983). It would be a matter of routine chemistry to excise these regions on the basis of published restriction maps for the virus in question and, if necessary, to modify the sites to enable or facilitate splicing the enhancer into the product gene or selection gene vector as desired. For example, see Kaufman et al., Mol. Cell Biol.2 pp. 1304–19 (1982). Alternatively, the enhancer may be synthesized from sequence data; the sizes of viral enhancers (generally less than about 150 bp) are sufficiently small that this could be accomplished practically.

The enhancer may be repeated within the vector, either in a tandem fashion (as is the case with the SV40 virus enhancer as found in nature) or separated throughout the vector at the sites discussed above. Preferably the enhancer is in the same orientation in relation to the product and/or selection gene as it was in relation to the gene under its influence in the wild-type source. The enhancer is preferably located upstream from any promoter present in the vector. A plurality of different enhancers may be employed, and the enhancer need not be ligated to either the product or selection gene to be useful in transformation. In an unlinked vector system the enhancer is preferably present on the vector containing the product gene. This will increase the probability that the product and selection genes will by physically linked in the cotransformants. About 10 to 50 times more transformants can be obtained in this fashion for a given amount of transforming DNA.

The enhancer need not contain any of the flanking sequences found in its wild-type environment, e.g. viral origins of replication or related promoter components such as TATA boxes, cap sites or transcription primer sequences. However, the absence of fortuitous restriction enzyme sites allowing for the deletions of these sequences may make it more convenient to include all or a portion of the sequences. Also, it can be more convenient to use a DNA fragment containing both an enhancer and the promoter normally under wild-type biological control of the enhancer.

Enhancer and enhancer-promoter regions also can be selected from eucaryotic cells rather than viruses. These are preferably enhancers associated with genes which produce protein in large constitutive amounts in the source cells. It has been found that they will similarly produce high yields of product from genes other than those normally controlled in the wild type environment. The host cell to be transformed is preferably a cell line of the same somatic or germ origin as the cell from which the enhancer was obtained. For example, the immunoglobulin gene activating or enhancing region in the $J_k$-$C_k$ intron can be introduced either upstream or downstream of the product gene, and the construct cotransfected with a selection gene into a myeloma cell line. See Gillies et al., "Cell"33:717–728 [1983] for further details on this enhancer.

Both the product gene and the selection gene will be ligated to promoters so as to be under the transcriptional control of a promoter, except in the linked vector embodiment disclosed above. The promoter may be the wild-type promoter for the gene in question, or the gene may be ligated to a promoter from another gene in the transformed cell line, from other eucaryotic cell lines or from eucaryotic viruses. Obviously, the promoter should be recognized by the host to be transformed (in the absence of fortuitous recombination with promoters in the transformed cells), but otherwise the choice of a promoter is not believed to be critical. Particularly desirable promoters are linked to 5' untranslated leaders and are transcriptionally or translationally activated by exogenous agents or conditions, e.g., accessory gene products (transcripts and polypeptides), heavy metal ions, heat shock or viral infection. A preferred promoter for product gene expression is the adenovirus major late promoter with the tripartite leader.

The vector system need not contain an enhancer if a promoter is chosen that is enhancer independent, e.g., the promoter for mouse alpha-globin. However, vectors with an enhancer and an enhancer dependent strong promoter, such as the adenovirus major late promoter, are employed in preference to such enhancer independent strong promoters. A strong promoter is one that results in the same or more transcripts than the SV40 early promoter under controlled conditions.

Another element which preferably should be present in the vector assembly is a polyadenylation site. This is a DNA sequence located downstream from the translated regions of a gene at which adenine ribonucleotides are added to form a polyadenylate tail at the 3' end of the messenger RNA. Polyadenylation is important in stabilizing the messenger RNA against degradation in the cell, an event that reduces the level of messenger RNA and hence the level of product protein.

Eucaryotic polyadenylation sites are well known. A concensus sequence exists among eucaryotic genes: the hexanucleotide 5'-AAUAAA-3' is found 11–30 nucleotides from the point in RNA at which polyadenylation starts. DNA sequences containing polyadenylation sites may be obtained from viruses in accord with published reports. Exemplary polyadenylation sequences can be obtained from mouse beta-globin, simian virus 40 late or early region genes, etc. Viral polyadenylation sites are preferred. Since these sequences are known, they can be synthesized in vitro and ligated to the vectors in conventional fashion.

A polyadenylation region should be located downstream from the product gene in linked or unlinked vectors. In unlinked vectors it is optionally ligated downstream from the selection gene. The sequence which separates the polyadenylation site from the translation stop codon is preferably an untranslated DNA region such as an unpromoted eucaryotic gene. The oligonucleotide preferably extends for a considerable distance, on the order of up to about 1,000 bases, from the stop codon to the polyadenylation site. This 3' untranslated nucleotide sequence generally results in an increase in product yields. The vector may terminate from about 10 to about 30 bp downstream from the concensus sequence, but it is preferable to retain the 3' sequences found downstream from the polyadenylation site in its wild-type environment. These sequences typically extend about from 200 to 600 base pairs downstream from the polyadenylation site.

It has been found that the presence of introns in the untranslated, transcribed portion of the vector can increase cotransformation product yields. Such introns may be obtained from other sources than either the host cells or the gene sources. For example, a 3' splice site from an immunoglobulin gene inserted into the untranslated region of the adenovirus major late transcript in place of a portion of this transcript's normal intron (as described more fully below) resulted in an increase in product yields.

Accessory DNA may be supplied as part of the transformation vector system. This is DNA which improves the stability of product synthesized by the transformant cell line, increases amplification of transfected genes or increases transcription or translation. This DNA contains functions that are recognized by the parental cell. As such it therefore serves as more than a mere carrier or bulking DNA used heretofore in transformations. One group of accessory DNA comprises DNA encoding translational activators. Translational activator genes produce protein or short, untranslated RNA products which interact with the messenger RNA for the product so as to increase the rate or efficiency of translation. An example is the adenovirus DNA which encodes virus-associated (VA) RNA (Thimmappaya et al., "Cell"31:543–551 [1982]. This DNA produces two species of small untranslated RNAs (VA 1 and VA 2). The RNA products of VA DNA are believed to associate with the tripartite leader sequence of the adenovirus major late promoter in a manner that is presently unclear to increase translation from mRNA containing the leader. VA 1 or VA 2 DNA is well known. It, along with its promoter, may be directly ligated into a linked vector (preferably upstream from the product gene promoter or downstream from the polyadenylation site) or may be transfected while unlinked to either the product or selection gene.

Another group of accessory DNA includes genomic eucaryotic DNA from the parental cell. This DNA is believed to include origins of replication or sequences that promote DNA stability, but the mechanisms responsible for the beneficial effects of such DNA are unknown. This DNA can be obtained by making a random shear or endonuclease digest of genomic DNA of the cell line. The DNA should contain fragments of a size ranging about from 50 to 5000 base pairs. These fragments are then ligated upstream from the transformation vector promoter (and preferably upstream from any enhancer) or downstream from the polyadenylation site at available restriction sites. These vectors are then suitable for transformation, whereafter the transformants are screened for one or more desirable characteristics, e.g., stability of product synthesis after serial culture of the transformant and/or high product yields.

The product yield from transformants can be improved by transforming the cells with accessory DNA termed trans-acting transcriptional activators. Such DNA encodes proteins or protein derivatives that stimulate transcription. One class of transcriptional activator is referred to as immortalizing genes in that they permit unlimited successive progeneration; cells containing such genes do not die after a given number of divisions. These activators do not need to be ligated into the same DNA strand as the product gene in order to increase transcription rates, and in this respect they differ from enhancers, Imperiale et al., "Cell"35:1-27–236 [1983], Green et al., "Cell"35:137–148 [1983]. Several candidates for trans-acting transcriptional activators are known and have been cloned. Examples include the C-myc, polyoma large T and adenovirus E1A genes.

Cells which are transformed with transcriptional activators, translational activators, and strong promoters or promoter-enhancers combinations offer the greatest potential for elevated product synthesis. A cascade effect will result from the transcriptional and translational activator-transformed cells.

The vectors preferably will be supercoiled, double stranded, circular constructs. This is the form in which the vectors are obtained from the standard procaryotic cloning procedures by which they are made. However, the vectors may be linearized, i.e. covalently cleaved at one point, incidental to other steps such as ligation to genomic accessory DNA.

The following table includes representative examples of suitable transformation vector systems.

TABLE 1

1. $\llcorner E_n$—VP—Pd—S—p(A)—R$\lrcorner$

2. $\llcorner E_{\overline{n}}$—VP—Pd—p(A)—R$\lrcorner$; $\llcorner$VP—S—p(A)—R$\lrcorner$ 3. GF—$E_n$—VP—Pd—p(A)—R—GF; GF—S—p(A)—R—GF 4. GF—EP—Pd—p(A)—GF; $\llcorner$EP—S—p(A)—R$\lrcorner$ 5. $\llcorner$VP—TTA—p(A)—R$\lrcorner$; $\llcorner E_{\overline{n}}$—VP—Pd—p(A)—R$\lrcorner$; $\llcorner$EP—S—p(A)—R$\lrcorner$ 6. $\llcorner$VP—TTA—p(A)—R$\lrcorner$; $\llcorner E_n$—VP—Pd—p(A)$\lrcorner$; $\llcorner$EP—S—p(A)$\lrcorner$ 7. $\llcorner$VP—TLA—p(A)—R$\lrcorner$; GF—TTA—$E_n$—VP—Pd—p(A)—GF; $\llcorner$EP—S—p(A)—R$\lrcorner$ 8. $\llcorner E_n$—VP—I—Pd—p(A)—R$\lrcorner$; $\llcorner$VP—S—p(A)—R$\lrcorner$;

9. $\llcorner$TLA—p(A)—R$\lrcorner$; $\llcorner$VP—TTA—p(A)—R$\lrcorner$; $\llcorner E_n$—Vp—I—Pd—p(A)—R$\lrcorner$; $\llcorner$EP—S—R$\lrcorner$;

10. $\llcorner E_{\overline{n}}$—VP—I—Pd—S—TLA—p(A)—R$\lrcorner$

11. $\llcorner$EP—Pd—B—S—$E_{\overline{n}}$p(A)—R$\lrcorner$; $\llcorner$VP—TLA—p(A)—R$\lrcorner$ 12. $\llcorner E_n$—VP—Pd$_1$—Pd$_2$—S—p(A)—R$\lrcorner$ 13. $\llcorner$TLA—VP—Pd—S—p(A)—R$\lrcorner$ 14. GF—TLA—VP—TTA—p(A)—R—GF—En—VP—Pd—I—p(A)—R—GF

TABLE 1-continued

15. 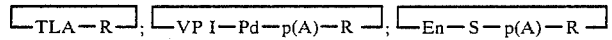

EP = nonviral promoter recognized by eucaryotic host cells
VP = viral promoter recognized by eucaryotic host cells
TTA = trans-acting transcriptional activator
$E_n$ = enhancer
TLA = translational activator
p(A) = polyadenylation site
Pd = product gene
S = selection gene
B = oligonucleotide bridge
— = phosphodiester bond
; = designates unligated vector components
GF = eucaryotic genomic fragment
I = exogenous intron
R = replication component (plasmid or bacteriophage residue from the synthesis vector)

 = designates a circularized DNA sequence, such as a plasmid.

Vector Synthesis

Linked vectors having short or no oligonucleotide sequences between the product and selection gene can be made in several ways. Ion the absence of a restriction site adjacent to the translatational stop codon for the product gene, or proximately downstream therefrom, the product gene could cut at a restrictions ite upstream of the wild-type translational stop codon and the codon then ligated to the selection gene fragment using synthetic linkers. Another way of making such a vector is by the use of a bridging nucleotide probe to delete undesirable sequences intervening between the product and selection gene, as is shown in Example 4 below. Alternatively, if the carboxy terminal amino acids of the product protein are not necessary for biological activity then a synthetic termination codon could be ligated to a convenient 3' terminus. Use of a gene fragment here is not a preferred embodiment because it usually is desired to synthesize product protein which is as identical as possible to that found in nature.

The 5' untranslated regions which flank the selection gene in its wild-type environment can be removed in the same fashion as described above for the product gene, and this can be accomplished simultaneously with the deletion from the product gene as shown in Example 4. However, it is unnecessary that the protein expressed by the selection gene or a derivative thereof be identical to the wild-type, e.g., more active towards a growth limiting substrate or more resistant to a toxin than the wild-type protein. In linked vectors the selection gene is preferably under the control of the product gene promoter. This will help to stabilize the cell's genotype and expression of product protein since cells which delete the product gene will not survive the selection agent in the absence of recombination events with the transformants. The opposite has been found to be the case with unlinked vectors, although here the same promoter can be used for both the selection and product genes.

Otherwise, the vectors described herein can be synthesized by techniques well known to those skilled in this art. The components of the vectors such as product or selection genes, enhancers, promoters, trans-acting transcriptional activators, translational activators and the like can be obtained from natural sources or synthesized as described above. Basically, if the components are found in DNA available in large quantity, e.g. components such as viral functions, or if they can be synthesized, e.g. polyadenylation sites, then with appropriate use of restriction enzymes, large quantities of vector can be obtained by simply culturing the source organism, digesting its DNA with an appropriate endonuclease, separating the DNA fragments, identifying the DNA containing the elements of interest and recovering same using techniques well known in the art. Ordinarily, a transformation vector can be assembled in small quantity and then ligated to a suitable autonomously replicating synthesis vector such as a procaryotic plasmid or phage. The pBR322 plasmid can be used in most cases. See Kaufman et al. (1982), supra. Larger transformation vectors may require high capacity synthesis vectors such as cosmids (a vector in which the DNA of a phage such as is packaged in the phage capsid but which replicates as a plasmid when transfected to a permissive host).

The synthesis vectors are used to clone the ligated transformation vectors in conventional fashion, e.g. by transfection of a permissive procaryotic organism, replication of the synthesis vector to high copy number and recovery of the synthesis vector by cell lysis and separation of the synthesis vector from cell debris by methods well known to those skilled in the art.

The resulting harvest of synthesis vector can be directly transfected into eucaryotic cells, or the transformation vector can be isolated from the synthesis vector by appropriate endonuclease digestion, separation by molecular weight and recovery of the transformation vector. Transformation vector isolation is not necessary so long as the remainder of the synthesis vector does not adversely affect eucaryotic gene amplification, transcription or translation. For example, the preferred synthesis vector herein is a mutant of the E. coli plasmid pBR322 in which sequences have been deleted that are deleterious to eucaryotic cells. See Lusky et al., Nature 293:79-81 [1981]. Use of this mutant obviates any need to delete the plasmid residue prior to cotransformation.

Cotransformation, Selection and Detection of Amplification

The cells to be transformed may be any eucaryotic cell, including yeast protoplasts, but preferably a non-fungal cell. Primary explants (including relatively undifferentiated cells such as stem cells), and immortal and/or transformed cell lines are suitable. Candidate cells need not be genotypically deficient in the selection gene so long as the selection gene is dominant acting.

The cells preferably are stable mammalian cell lines as is discussed above. Cell lines that are known to stably integrate selection genes into their chromosomal DNA are best, for example Chinese hamster ovary (CHO) cell lines. Also useful in the practice of this invention are HeLa, COS monkey cells, melanoma cell lines such as the Bowes cell line, mouse L cells, mouse fibroblasts, mouse NIH 3T3 cells, and the like.

Cotransformation with unlinked vectors can be accomplished serially or simultaneously, (see U.S. Pat. No. 4,399,216). Methods for facilitating cellular uptake of DNA are described above. Microinjection of the vector into the cell nucleus will yield the highest transformation efficiencies, but exposing parental cells to DNA in the form of a calcium phosphate precipitate is most convenient. Considerably better cotransformation efficiencies result from cotransformation with a molar excess of product to selection gene, preferably on the order of 100:1 or higher.

The population of cells that has been exposed to transforming conditions is then processed to identify the transformants. Only a small subpopulation of any culture which has been treated for cotransformation will exhibit the phenotype of the selection gene. The cells in the culture are screened for the phenotype. This can be accomplished by assaying the cells individually with a cell sorting device where the phenotype is one that produces a signal, e.g. cell surface antigens or fluorescence upon cleavage of a fluorogenic substrate by an enzyme produced by the selection gene. Preferably, however, the phenotype enables only transformants to grow or survive in specialized growth media as is further dicussed above.

Selection transformants then are screened for ligation of the product gene into their chromosomes or for expression of the product itself. The former can be accomplished using Southern blot analysis, the latter by standard immunological or enzymatic assays.

Once the transformants have been identified, steps are taken in accord herewith to amplify expression of the product gene by subcloning in the presence of a selection agent in constant or increasing amounts. Generally this entails taking the transformant cell population and (a) selecting one or more cells from the cell population that express the product in a preferential fashion when compared to other cells in the population, (b) culturing the selected cell or cells to a subsequent cell population under conditions designed to select for a change in the expression of the phenotype, and (c) further selecting one or more cells from the subsequent cell population that express the product in a preferential fashion when compared to other cells in the subsequent population. Step (b) advantageously is conducted with a plurality of the step (a) clones.

Typically, one exposes a culture of parental cells to quantities of vector DNA under conditions known in the art to enhance DNA uptake, e.g., the methods such as uptake of DNA precipitates as are described above. This culture then is diluted and plated onto tissue culture dishes which contain growth medium and the selection agent. The individual cells which survive the selection agent form visible colonies on the dishes. These initial transformants are removed and serially cultured en mass in the presence of increasing amounts of selection agent. The final culture (usually the third or fourth) is diluted into a selection agent-containing medium so that a convenient volume will only contain one cell, the volume aliquots distributed into wells in microtiter plates and the plates cultured. Clones will be present in most of the wells. The culture medium in each well is assayed for product to identify the high-yielding clones which have amplified the product and selection genes.

The same process can be conducted with a single initial transformant clone.

The process set forth in steps (a) through (c) above can be repeated over and over until an optimal cell line is obtained. The ultimate objective is to obtain a cell line which exhibits desirable characteristics not possessed by the prior lineage. Especially desirable are transformants which are genotypically stable as to the product gene, e.g., (1) which are not susceptible during culture to deletion of the product gene even in the absence of the selection agent, (2) which express maximal quantities of product and (3) which have attractive growth characteristics, e.g. a rapid growth rate and less fastidious nutritional requirements.

This subcloning method takes advantage of the normal genetic fluidity within transformants. Exogenous DNA is continuously translocated or deleted through various natural recombinational events, although this activity decreases in intensity after extensive serial culture under set selection conditions. This may be considered by the art to be a disadvantage, since it frequently leads to deletion of exogenous genes. It now has been found in accord with the invention herein that such events result in high-yielding, stable cell lines. Such transformants are screened from cell populations grown in the present of a selection agent. This is accomplished by simply assaying individual cells from such cultures and selecting those having the desired characteristics. Usually one will select the high-yielding cells from each culture.

This process is repeated through successive cycles of steps (a) through (c), preferably from about 2 to about 10 cycles. After further culture in the presence of the selection agent, individual daughter cells that exhibit heterogeneity as to the expression of the product gene can be selected from the culture population. In this fashion it has been possible to increase transformant product yield substantially, on the order of 100 to 1,000 fold. Successive cycles can be interrupted by culture in the absence of the selection agent.

This process is to be distinguished from the prior art process of selecting a given cell culture, growing an aliquot of this culture again under selection conditions, taking another random aliquot and culturing again under selection ad infinitum. The typical prior art process, which does not focus on selecting individual cells having desirable characteristics, merely serves to select daughter cells ultimately most adapted to survive under the applied selection conditions. These cells are not necessarily those which will produce the greatest product yield or have other desirable characteristics beyond survival.

The starting cultures used in this subcloning process may be single cells, cloned cultures of single starting cells or pools of selected cells or clones.

Transformants may be selected at any point in the subcloning process by chromosomal karyotyping. Such chromosomal structure has been found to be material in predicting transformant resistance to deletions or rearrangements leading to product yield losses. Cells generally are most stable that display chromosomal structures akin to the pretransformed parent cells and where the DNA coding for the product is found in relatively few chromosomal sites. On the other hand, cells should not be selected which contain extra chromosomes (such as double minute chromosomes), broken chromosomes, translocated chromosomal segments or chromosomes of supranormal length. Chromosomal photomicrographs of selected cells can be made in conventional fashion.

The cells obtained after subcloning should be maintained in the presence of their selection agent, at least in seed cultures. The cells may be stored in the same way as eucaryotic cells of the transformant type. Scale-up culturing for the synthesis of product on a commercial scale is accomplished in conventional ways, e.g. surface or suspension culture in defined media. It is not preferable to scale-up in the presence of the selection agent unless the agent is innocuous to the organism to which the product is to be administered or unless the product is not intended for therapeutic purposes. In the case of tissue plasminogen activator (tPA), culturing under conditions that select for product gene uptake and amplification, e.g., under increasing concentrations of methotrexate (MTX), high tPA expression causes the cells to become spherical and detach from surfaces to which they adhere.

This phenomenon has been demonstrated to be proximately caused by the plasminogen found as a protein constituent in the animal serum present in many eucaryotic culture media. tPA converts plasminogen to plasmin, and the plasmin hydrolyzes cell surface protein, thereby adversely affecting cell growth and yield. Accordingly, the culture medium to be used with tPA-synthesizing transformant eucaryotic cells (cells having parental cell lines not synthesizing human tissue plasminogen activator) will be a medium that does not generate proteolytic activity, especially plasmin activity, in the present of human tPA. This may be accomplished by several techniques. First, cell culture medium which is essentially free of plasminogen may be used. The medium can be essentially free of serum, W. G. Hamilton et al., "In Vitro" 13 537-547 [1977] or plasminogen and other proteolytic enzymes and proenzymes may be removed from the medium or its serum components by passage through a column of lysine-coupled Sepharose in accord with known techniques for fractionating proteins. Alternatively, an essentially plasminogen-free protein fraction such as human albumin or a suitable cohn fraction can be used in place of serum and plasma.

Second, a protease, especially plasmin, inhibitor may be added to the medium. Alpha-2-antiplasmin is a suitable example. Other more non-specific protease inhibitors such as phenylmethylsulfonylfluoride (PMSF) or aprotinin may be included in the medium. Such inhibitors can be separated from the tPA culture medium incident to later tPA purification procedures or by dialysis of the tPA-containing culture medium.

The above techniques can be used singly or in combination, but it is most preferred to use eucaryotic culture medium which is essentially free of plasminogen. "Essentially free" means that the level of plasminogen is sufficiently low that tPA synthesis does not adversely affect cell physiology.

Cotransformants which may be produced in accordance with the processes described herein are suitable for in vivo transfections of higher organisms in accordance with known techniques (U.S. Pat. No. 4,396,601). Primary explants or stable cell lines from a potential host animal are cotransformed and inoculated into the host or a substantially otherwise syngeneic host which is genotypically deficient in the product protein. This use of the cotransformant is particularly suitable for genetic deficiency diseases such as hemophilia, where antihemophilic factor (AHF)-expressing transformants will be particularly beneficial.

BRIEF DESCRIPTION OF THE DRAWINGS

FIG. 1 is the nucleotide sequence for human tissue plasminogen activator (tPA) and a portion of its noncoding flanking regions.

FIGS. 3a-3b are schematic representations of a method for preparing tPA cotransformation vectors.

Figure 2A:
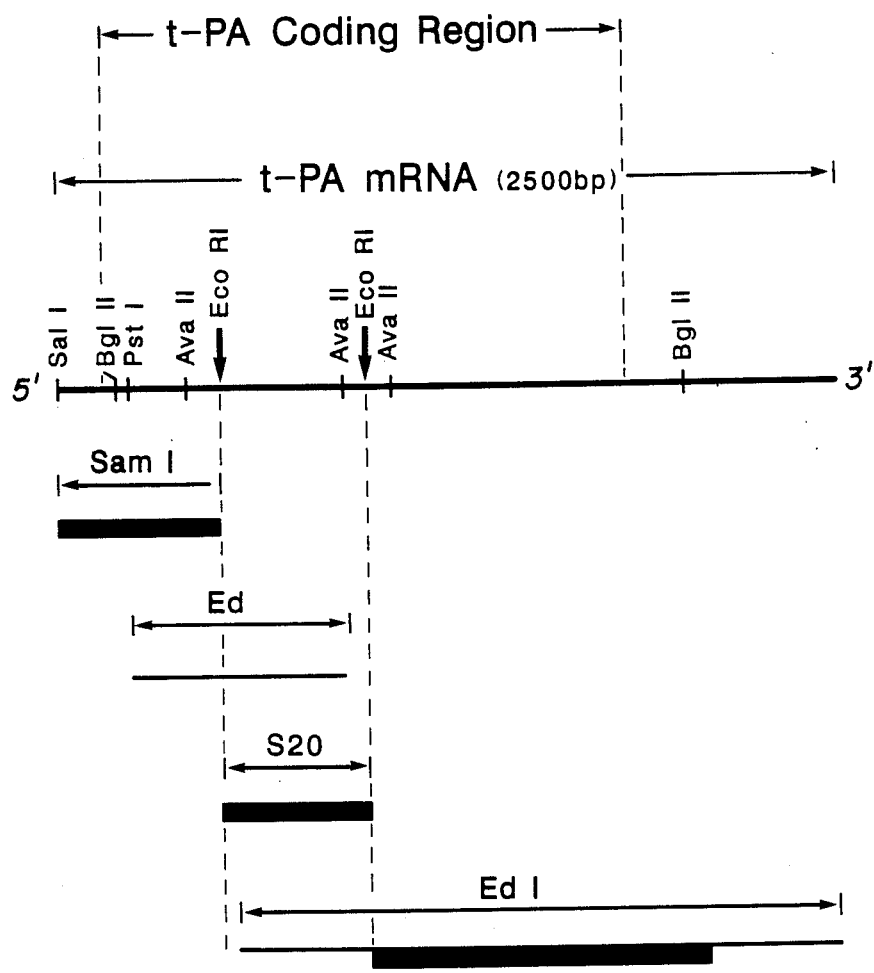
FIG. 2a is an illustration of four overlapping cDNA clones that encode the entire tPA protein sequence.

The following examples are considered to be merely illustrative and are not intended to imply any limitation on the scope of the claims. In the examples, degrees centigrade are used.

EXAMPLE 1 cDNA Encoding Tissue Plasminogen Activator (Human)

The cDNA gene for encoding human tPA was obtained by reverse transcription from mRNA isolated from the Bowes melanoma cell line in accord with conventional procedures previously employed with other cells containing large quantities of desired mRNA.

tPA protein was isolated from the Bowes melanoma cell line (available from Dr. Rifken, New York University). Amino acid sequence analysis showed that the protein found in conditioned medium from Bowes melanoma cells contained two distinct N-termini, one N terminus containing three amino acids more than the other. These two N-termini are referred to as the glycine N-terminus (Gly - Ala - Arg - Ser - Tyr - Gln - Val - Ile - Cys - Arg - Asp - Glu - Lys - Thr - Gln - Met - Ile -Tyr Gln - Gln - His) and the serine N-terminus (Ser - Tyr - Gln - Val - Ile - Cys - Arg - Asp - Glu - Lys - Thr - Gln - Met - Ile - Tyr - Gln - Gln - His).

Messenger RNA was isolated from Bowes melanoma cells and used as a template for the synthesis of cDNA as is generally known in the art. The cDNA was copied to produce a double strand. It was introduced into tetracycline resistant plasmid vectors by homopolymeric tailing or synthetic linkers as is well known in the art. Libraries of cloned plasmids, each clone containing a unique cDNA copy of a mRNA species present in the Bowes melanoma cells, were prepared by transformation of *E. coli* with the vectors and selection of antibiotic resistant *E. coli* cells.

Figure 1A:
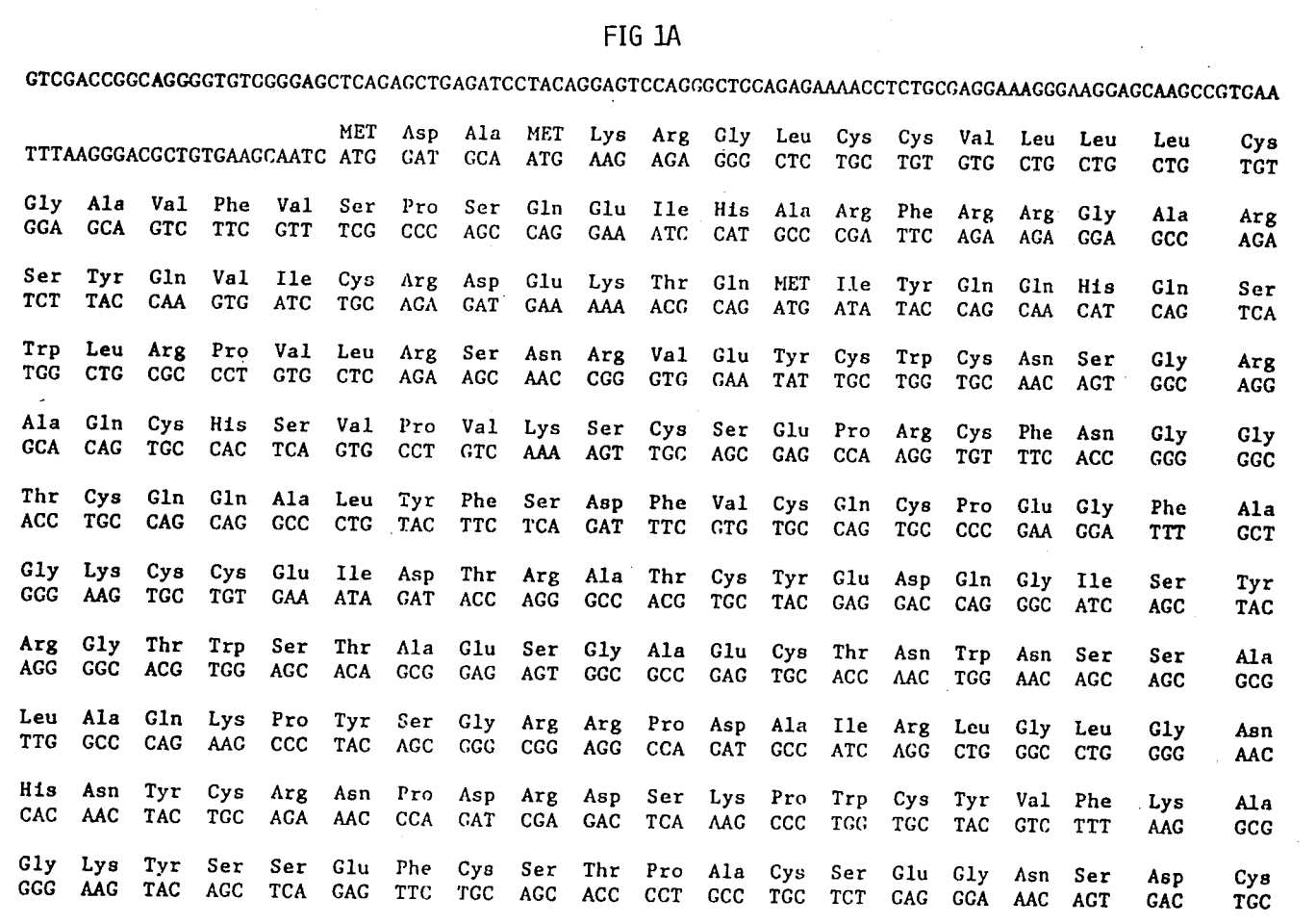

Plasmids in the cDNA libraries which contain cDNA encoding at least part of tPA were identified by the standard Grunstein and Hogness screening method (Grunstein et al., 1975 PNAS 72 3961). In this method, DNA is immobilized in a single stranded form and screened for the ability to hybridize or bind to radiolabelled probes. Such probes are short DNA oligonucleotides having a sequence consistent with the amino acid sequence of a small portion of the tPA protein. The amino acid sequence of amino acids 15-20 from the N-Terminus of tPA was used (designated in FIG. 1). Since some of these amino acids are encoded by more than one trinucleotide codon, a pool of 17-mer probes covering all the possibilities was prepared following standard procedures. A cDNA library was then screened by the method of Grunstein and Hogness until a clone in the library was found that hybridized to the probe. Confirmation that the clone encoded a portion of tPA was obtained by the routine procedure known as partial dideoxy primer extension, which determines the sequence upstream of the primer (Wallace et al., "Nuc. Acids Res." 9 3647-3656 [1981]). This demonstrated the clone contained codons corresponding to the N-terminal amino acid sequence of tPA.

The cDNA present in the clone that was found was isolated from the plasmid, radiolabelled, and used in turn as a probe to identify other overlapping fragments of tPA cDNA found in the cDNA library. This process was continued until fragments were identified which together (excluding the duplicate, overlapping sequences), encoded the mature tPA protein and portions of the untranslated 5' and 3' regions.

Two different libraries were screened to yield cDNA clones that together covered the entire coding sequence for tPA. cDNA clones Sam1 and S20 were isolated from an asymmetric-linkered library. This library was made following conventional procedures (Maniatis et al., Molecular Cloning—A Laboratory Manual, Cold Spring Harbor Laboratories, Cold Harbor, N.Y. (1982) in which cDNA from Bowes cell mRNA was ligated to EcoRl linkers at the 3' end and SalI linkers at the 5' end, and the linkered cDNA inserted into appropriate vectors. cDNA clone Ed1 was isolated from a GC-tailed cDNA library (Maniatis et al, supra). FIG. 2a illustrates that cDNA clones Sam1, S20, and Ed1 comprise a partially overlapping set which spans the entire coding sequence of tPA.

Figure 2B:
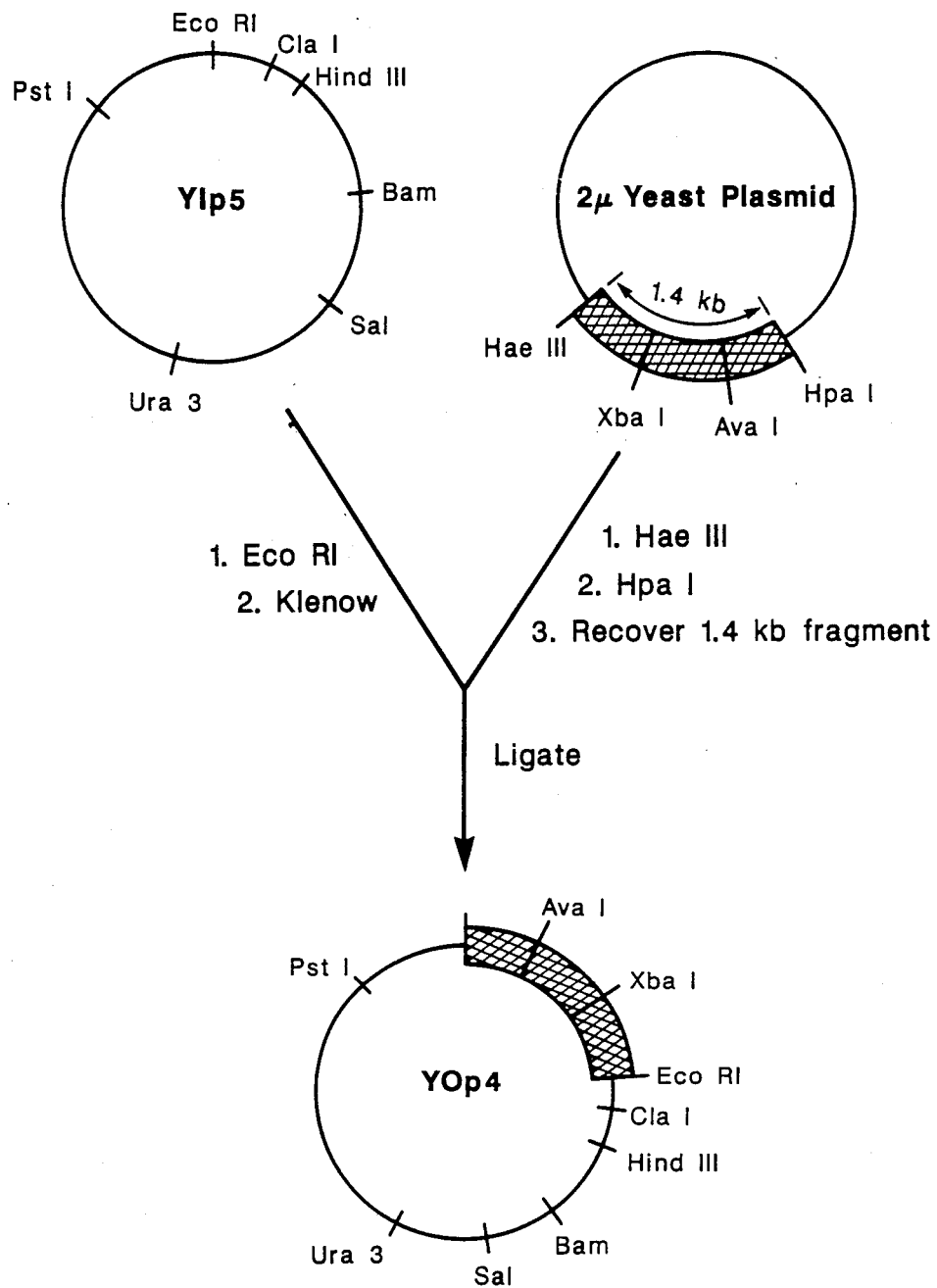
FIGS. 2b-2d are a schematic representation of a suitable method for obtaining replicative form cDNA for human tPA.
Figure 2C:
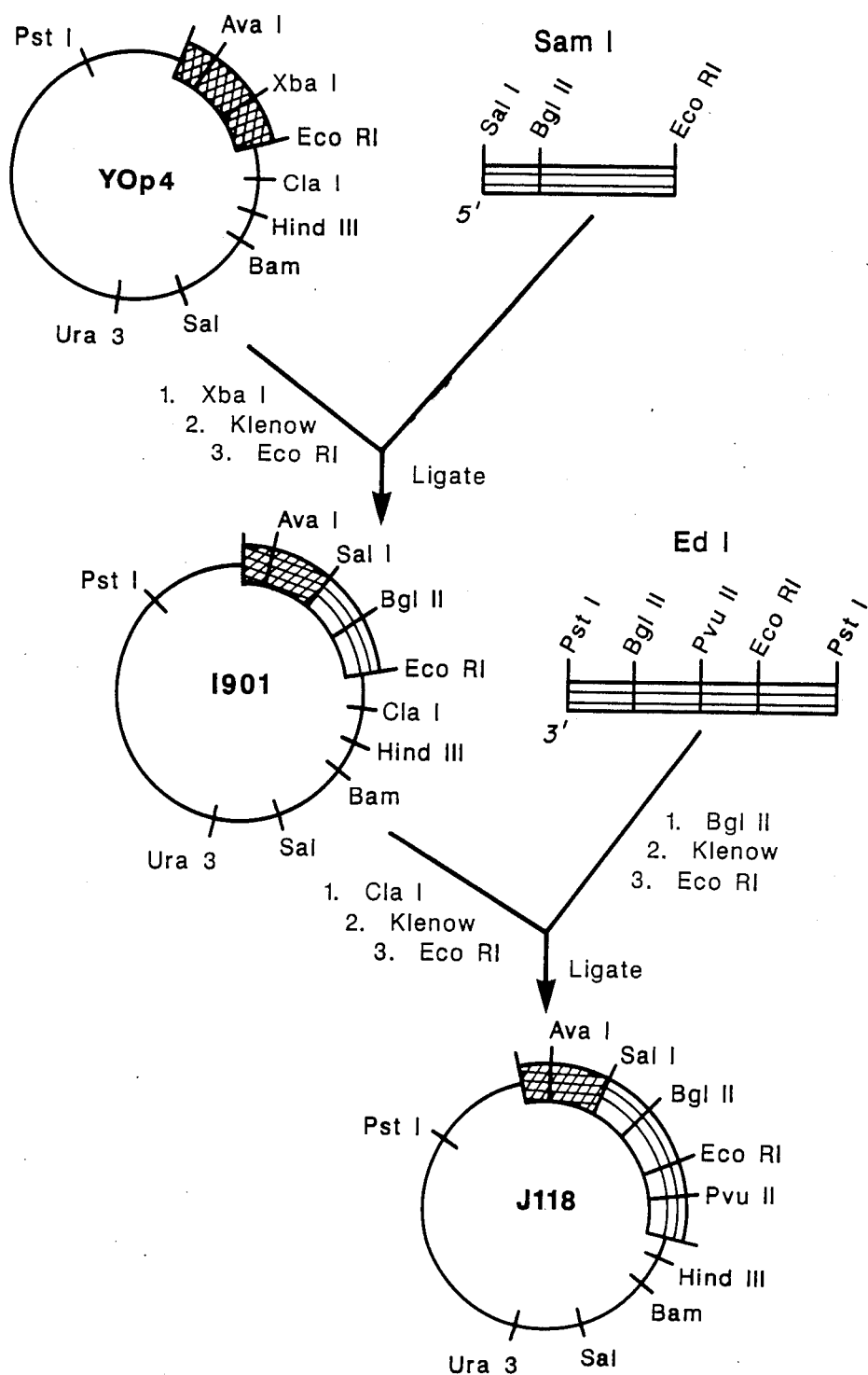
Figure 2D:
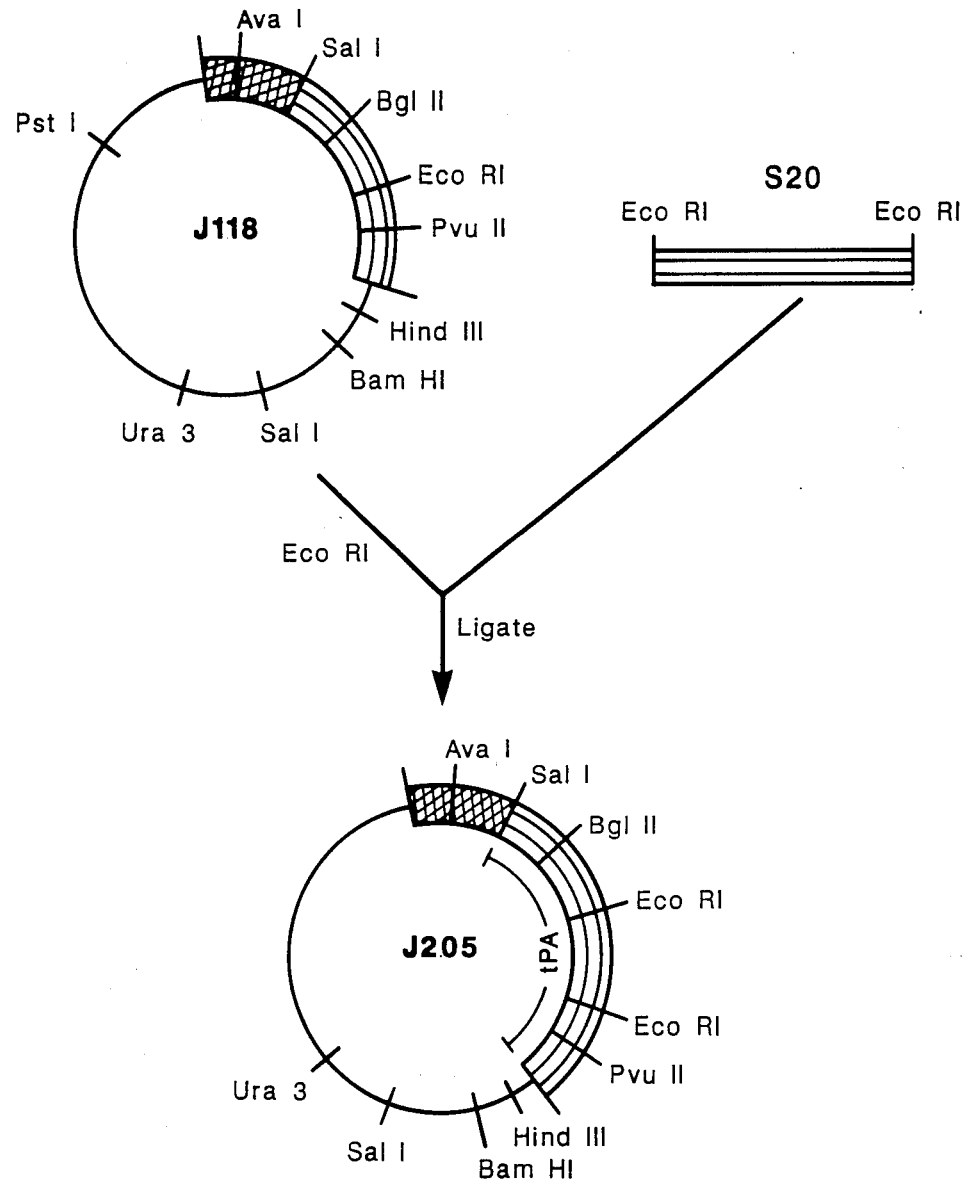

The technique which was employed to join together a single coding sequence from the three fragments is shown schematically in FIG. 2b, 2c, and 2d. FIG. 2b illustrates the construction of the plasmid used to receive the fragment, and for replication of the complete cDNA gene. The construction of plasmid YIp5 is disclosed by Botstein et al., "Gene" 8:17-24 [1979]. The 2μ yeast plasmid is commercially available. The designations + indicate restriction enzyme sites in the plasmids. Treatment with restriction enzymes and/or the Klenow fragment of DNA polymerase I (hereinafter sometimes referred to as "Klenow") is indicated by designations next to the arrows. These enzymes are commercially available. Conventional enzyme reaction conditions were employed. Note that ligation of the digestion products of certain restriction enzymes will result in a DNA sequence which is not hydrolyzable by either restriction enzyme. For an example see the elimination of the HpaI site upon construction of the YOp4 plasmid. FIGS. 2c and 2d illustrate the construction of a plasmid containing the full length cDNA clone from the three cDNA fragments identified in the libraries. In FIG. 2c the plasmid YOp4 is cleaved with XbaI, the ends made flush with Klenow and the linear plasmid cleaved again with EcoRl The tPA cDNA fragment containing the 5' end of the gene (including a portion of the untranslated 5' end-see the boxed SalI site in FIG. 1) was isolated from its plasmid by digestion with SalI, treatment with Klenow, and digested with EcoRl. Linear YOp4 and the tPA cDNA 5' fragment Sam 1 were ligated to form plasmid I901 with the formation of a SalI site upon ligation of the XbaI and SalI sites. Plasmid I901 was replicated in *E. coli* and screened for ampicillin resistance.

Plasmid I901 then was treated as shown in FIG. 2b and ligated to the 3' fragment (Ed 1) of tPA cDNA (rescued from its plasmid by successive Bgl II, Klenow and EcoRl treatment). The BglII site, designated in FIG. 1 by a box, is destroyed by ligation to the ClaI digest of plasmid I901. The PstI—BglII and EcoRI—PstI subfragments of the tPA cDNA are discarded without effect, in the first case because the region is noncoding, in the second because the region overlaps the third fragment, S20 (FIG. 2c), which supplies the discarded sequence. These steps yield the plasmid J118, which was replicated in *E. coli* and screened for ampicillin resistance.

Plasmid J118 was cleaved with EcoRl and ligated to the central tPA cDNA fragment S20 as shown in FIG. 2c. Proper orientation of the S20 fragment in J205 was confirmed by asymmetric endonuclease digestion as is known generally in the art.

The tPA cDNA gene had the nucleotide sequence shown in FIG. 1. This sequence differs from the previously published sequence of human tPA by a number of nucleotides and one amino acid substitution.

EXAMPLE 2

Construction of Transformation Vector

The starting plasmid in this Example is known as pAdD26SVp(A)3 (Kaufman et al., Mol. Cell Biol. 2(11):1304-1319 [1982]). It has the structure described in FIG. 3a. Briefly this plasmid contains a mouse dihydrofolate reductase (DHFR) cDNA gene that is under transcriptional control of the adenovirus 2 (Ad2) major late promoter. A 5' splice site is included in the adenovirus DNA and a 3' splice site, derived from an immunoglobulin gene are present between the Ad2 major late promoter and the DHFR coding sequence. The SV40 early polyadenylation site is present downstream from the DHFR coding sequence. The procaryotic-derived section of pAdD26SVp(A)3 is from pSVOd (Mellon, P., Parker, V., Gluzman, Y. and Maniatis, T. 1981, Cell 27:279-288) and does not contain the pBR322 sequences known to inhibit replication in mammalian cells (Lusky, M., and Botchan, M. 1981, Nature (London) 293:79-81.

pAdD26SVP(A)3 is converted into plasmid pCVSVL2 by the first step shown in FIG. 3a. The Ava II D fragment of SV40 was obtained by digesting SV40 DNA with Ava II, ligating Xho 1 linkers to the fragments, digesting with Xho 1 to open the Xho 1 site, and isolating the fourth largest (D) fragment by gel electrophoresis. Insertion of the linkered D fragment as shown in the first step yielded single direct repeat of the SV40 enhancer. This was the result of proportioning the amount of pAdD26SVp(A)3 to Xho-1 linkered D fragment in the ligation. The orientation of the SV40 D Fragment in pCVSVL2 was such that the SV40 late promoter is in the same orientation as the adenovirus major late promoter.

pCVSVL2 is converted into plasmid pB2L2 by a three step process designed to make it compatible for splicing with the J205 tPA gene from Example 1. First, one of the two PstI sites in pCVSVL2 is deleted by a partial digestion with PstI (using a deficiency of enzyme activity so that a subpopulation of linearized plasmids can be obtained in which only one PstI site is cleaved), then treatment with Klenow, ligation to recircularize the plasmid, transformation of *E. coli* and screening for deletion of the PstI site located 3' of the SV40 polyadenylation sequence.

Second, the plasmid was digested with BglII, treated with Klenow, ligated, and *E. coli* transformed colonies screened for destruction of the BglII site in the immunoglobulin intron (3' splice site in FIG. 3a).

Third, the PstI site was converted to a BglII site by digestion with PstI, Klenow treatment, ligation to BglII linkers and digestion with an excess (100 units/ug DNA) of BglII. The resulting linear DNA was isolated by gel electrophoresis in a low melting agarose (1.2%) gel in Tris-acetate buffer. This DNA was ligated in vitro at a concentration of one μg/ml at 24° and used to transfect *E. coli* HB101 (see Maniatis, et al, supra). Colonies resistant to tetracycline were grown and DNA prepared and analyzed for the presence of the BglII site at the 5' end of the DHFR cDNA by digestion with BglII and PvuII, and PstI digestion. Large scale preparations of DNA were performed by banding the DNA twice in CsCl.

pJ205 from Example 1 was digested with Hind III and SalI, treated with Klenow and ligated to BamHI linkers.

The resulting DNA was phenol extracted, chloroform extracted, and ethanol precipitated by the addition of sodium acetate, (pH 4.5) to 0.3 M and 2.5 vol. of ethanol. The DNA was recovered by centrifugation, the pellet dried. The pellet was resuspended and digested with BamHI (100 units/ug of DNA) in order to cleave the BamHI linkers. The digest was applied to an agarose gel and the 2.1 kb band identified. The band was recovered and the DNA obtained by adding an equal volume of a buffer containing 10 mM Tris HCl (pH 7.4) and 1 mM EDTA, and heating for 15' at 68°. Then the DNA is phenol extracted (2×), chloroform extracted (2×), and ethanol precipitated by addition of sodium acetate (pH 4.5) to 0.3 M and 2.5 volumes of ethanol.

Figure 3B:
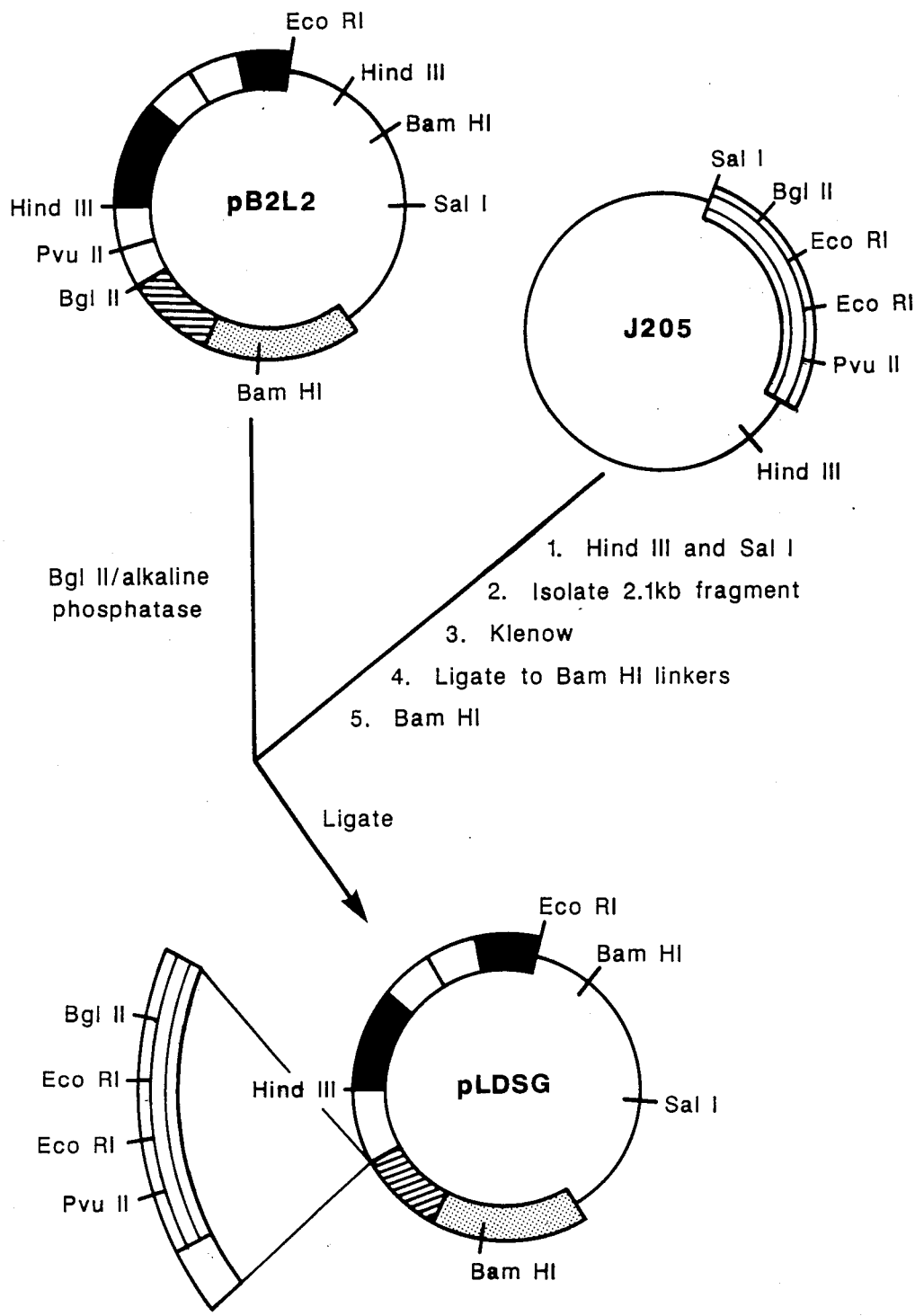

As illustrated in FIG. 3b, vector pB2L2 was digested with BglII, treated with bovine alkaline phosphatase, extracted with phenol (2×), chloroform (2×), and ethanol precipitated by the addition of NaOAc (pH 4.5) to 0.3 M and 2.5 volumes of ethanol. This precipitated DNA was ligated to the BamHI linkered 2.1 kb fragment from pJ205. The ligated DNA was used to transform *E. coli* HB101. Colonies which were tetracycline resistant were screened with a $^{32}P$ labelled probe specific to the tPA cDNA by the Grunstein-Hogness procedure. The probe was made by digestion of J205 with Hind III and SalI, and then labelled with T4 DNA polymerase utilizing $^{32}P$-alpha-dCTP. DNA was prepared from positively hybridizing clones and screened for the presence to the tPA cDNA by separate restriction enzyme digestion with Hind III, Pvu II and SacI. These digests demonstrated not only the presence of the tPA cDNA in the vector but also the orientation of the cDNA with respect to the promoter. pLDSG is a plasmid that contains tPA in the proper orientation.

EXAMPLE 3

Cotransformation and Amplification plasmids pLDSG and pAdD26SVp(A)3 (Example 2) were mixed together (50 μg pLDSG and 0.5 μg pAdD26SVp(A)3 and precipitated by the addition of NaOAc (pH 4.5) to 0.3 M and 2.5 vols. of ethanol. Precipitated DNA was allowed to air dry, was resuspended in 2X HEBSS (0.5 ml) (Chu and Sharp "Gene" 13:197-202 [1981]) and mixed vigorously with 0.25 M CaCl₂ (0.5 ml) as described (Kaufman and Sharp, "J. Mol. Biol." 150:601-621 [1982]). The calcium-phosphate-DNA precipitate was allowed to sit 30' at room temperature, and applied to CHO DUKX-Bl cells (Chasin and Urlaub, P.N.A.S. 77:4216-4220 [1980]). The growth maintenance of these cells has been described (Kaufman and Sharp, "J. Mol. Biol." supra and Chasin and Urlaub, supra).

The DUKX-Bl cells are subcultured at $5 \times 10^5/10$ cm dish for 24 hours prior to transfection. The media is removed, and the DNA-calcium phosphate precipitate is added to the monolayer. After 30 minutes incubation at room temperature, 5 ml of alpha-media (Flow) with 10% fetal calf serum was applied and the cells were incubated at 37° for 4.5 hr. The media was then removed from the monolayer of cells, 2 ml of alpha-media (Flow) containing 10% glycerol was added for 3' at room temperature (24° C.) and then removed and the cells rinsed and fed with alpha-media containing 10% fetal calf serum, 10 μg/ml each of thymidine, adenosine, deoxyadenosine, penicillin and streptomycin. Two days later the cells were subcultured 1:15 into alpha media with 10% dialyzed fetal calf serum, penicillin and streptomycin, but lacking the nucleosides. Cells were then fed again with the same selective media (lacking nucleosides) after 4-5 days.

Colonies appear 10-12 days after subculturing into selective media. Two schemes for methotrexate (MTX) selection and amplification have been followed. In the first scheme depicted in Table 2 below, single independent cloned transformants are isolated on the basis of uptake of the exogenous DNA (selection gene) and subsequently each clone is propagated under conditions to increase expression of the product gene i.e., growth in increasing concentrations of methotrexate. In the second scheme a pool of multiple independent transformants are isolated on the basis of uptake of the exogenous DNA (selection gene) and are propagated under conditions to increase expression of the product gene, i.e. growth in increasing concentrations of methotrexate. Then individual clones are isolated from the mass selected population and analyzed for expression of the product gene. Those clones exhibiting highest levels of product gene expression are grown again under conditions to further increase product expression (i.e. growth in increasing concentrations of methotrexate in the culture media).

Results following Scheme 1 are shown in Table 3 below. Individual clones capable of growth in alpha-media without nucleosides were selected, propagated and assayed for tPA activity. Activities are recorded as CTA milliunits/cell/day, i.e. mU/cell/day. (See below). Clones exhibiting tPA activity were subsequently selected for sequential resistance to 0.2 μM MTX, 0.1 μM MTX and 0.5 μM MTX.

Clone 4Cl did not synthesize increasing tPA activity under MTX selection. However, 4Cl was cultured in the absence of MTX to generate subclones (H3B and BlOA) which do coamplify and express high levels of tPA when selected for MTX resistance. Without wishing to limit the method herein to a particular hypothesis, this is thought to be due to the segregation of DHFR genes unlinked to tPA genes in siblings from the original 4Cl transformant. Subclones which contain a single DHFR gene linked to tPA genes amplify the DHFR and tPA genes together in these clones upon MTX selection.

TABLE 2

Schemes for Optimizing Product Expression

Scheme 1        Scheme 2

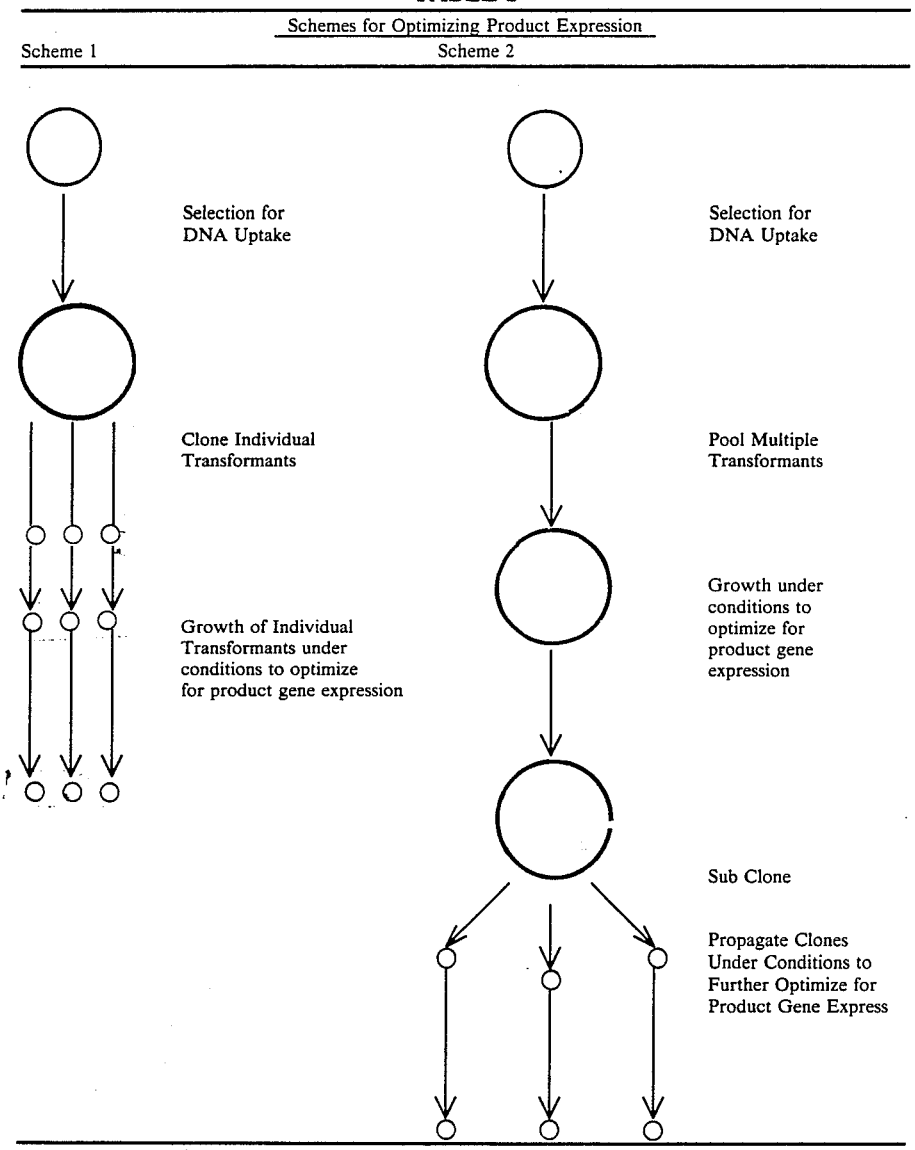

Scheme 1: Selection for DNA Uptake → Clone Individual Transformants → Growth of Individual Transformants under conditions to optimize for product gene expression Scheme 2: Selection for DNA Uptake → Pool Multiple Transformants → Growth under conditions to optimize for product gene expression → Sub Clone → Propagate Clones Under Conditions to Further Optimize for Product Gene Express

TABLE 3 tPA Activity (mU/cell/day) in clones selected for MTX resistance

| | uM MTX Concentration | | | |
|---|---|---|---|---|
| | 0 | 0.02 | 0.1 | 0.5 |
| Clones | | | | |
| 1E2 | .02 | .015 | .005 | .005 |
| 4D2 | .015 | .0015 | .003 | .002 |
| 2D5 | .01 | .04 | .04 | .025 |
| 4Cl | .04 | .03 | .035 | .03 |
| 4Cl Subclones | | | | |
| H3B | .09 | .26 | 1.0 | — |
| B10A | .025 | .09 | .19 | — |
| H8B | .02 | .045 | .035 | — |
| H12B | .05 | .15 | .005 | — |
| D8B | .08 | .095 | — | — |

Results following scheme II are shown in Table 4. A pool of about 300 of the colonies obtained from subculture on selection in media lacking nucleosides was made (the colonies from four selection plates). These transformants were selected for sequential resistance to 0.02 μM MTX and 0.05 μM MTX. Although the original pooled transformants contained tPA activities of 0.03, 0.9 and 1.9 mU/cell/day upon culture in media containing 0, 0.02 and 0.5 μM MTX, respectively, individual clones within the population expressed tPA in the amounts shown in Table 4. Individual clones varied 50 fold in levels of tPA expression from 0.2 mU/cell/day up to 10 mU/cell/day. This scheme is preferred for rapidly identifying clones which express large tPA activities. Obviously, Scheme I can be combined with Scheme II to yield even more prolific transformants.

TABLE 4

| | tPA Activity mU/Cell/Day |
|---|---|
| 300 Transformants Selected for Growth in alpha-media without nucleosides | 0.03 |
| ↓ | |
| Cells Selected for Growth in 0.02 uM MTX | 0.9 |
| ↓ | |
| Cells Selected for Growth in 0.05 uM MTX | 1.9 |
| ↓ | |

TABLE 4-continued

| Clone: in 0.05 uM MTX | tPA Activity mU/Cell/Day |
|---|---|
| #3 | 4.25 |
| 4 | 7.0 |
| 5 | 1.6 |
| 9 | 3.5 |
| 12 | 6.25 |
| 13 | 1.55 |
| 16 | 0.2 |
| 18 | 0.3 |
| 20 | 10.0 |

Monitoring tPA Expression

Sensitive assays for tPA exists which monitor the tPA catalyzed conversion of plasminogen to plasmin in the presence of fibrin. Plasmin may be detected by the release of $^{125}$I-fibrin fragments from $^{125}$I-fibrin which has been immobilized to a plastic plate (Astrup et al., Acad. Biochem. & Biophys. 40:340-351 [1952]), or by the cleavage of a chromogenic substrate (Drapier et al., Biochimie 61:403-471 [1979]. A suitable chromogenic substrate, designated S2251, is obtained from Kabi Diagnostics, Inc., Greenwich, Conn. These assays are well known to those versed in the art and are referenced in Astrup et al., supra and in Drapier et al., supra. tPA activity was measured by rinsing a plate of cells ($4 \times 10^5$ cells/10 cm plate) with 5 ml of serum free media and then applying 4 ml of serum free media. Cells were allowed to incubate 20 hours at 37° and samples in the conditioned media were taken for assay. Measurements of activity are expressed as the number of milliunits (mU) per cell per day. Under these conditions of assay, the Bowes melanoma cell line produces 0.02 mU/cell/day. The specific activity of the human tPA is 100,000 units/mg. The rate of cleavage of the $^{125}$I-fibrin or the S2251 substrate is directly related to amount tPA catalyzed conversion of plasminogen to plasmin. Samples of conditioned media from cells lacking tPA expression generate negligible backgrounds in these assays. This negligible background is due to proteases which are not fibrin activated since the background in the chromogenic substrate assay does not change with the elimination of fibrin from the standard assay In contrast, the activity from tPA producing CHO cell lines does exhibit fibrin activation very similar to that exhibited by the Bowes melanoma tPA. Quantitation of the tPA activity is obtained by comparison to a standard curve utilizing urokinase (Leo Pharmaceuticals, Belgium). A unit (CTA, Committee on Thrombolytic Agents) of activity is defined by comparison to the WHO standard reference preparation of urokinase. (Johnson et al., Thromb. Diath. Haemorrh 21, p. 259 (1969)).

The synthesis of tPA is monitored by twice rinsing a monolayer of cells ($2 \times 10^6$/10 cm) with 5 ml methionine free media and adding 1 ml of methionine free media containing lmCi $^{35}$S methionine. Cells were incubated 4 hours at 37° and the conditioned media was assayed by immune precipitation with rabbit anti-human tPA utilizing Staphylococcus aureus as the immunoadsorbant.

Results from gel electrophoresis of total labelled secreted protein from clone H3B indicate the only major difference in the secreted protein between the original H3B subclone propagated in a media without nucleosides and H3B cells selected for growth in 0.1 μM MTX is the presence of a strong band migrating at 67,000 daltons. This band is specifically immunoprecipitated with a rabbit-anti-human tPA antibody and comigrates with tPA similarly prepared from the Bowes melanoma cell line. These results indicate that upon selection of clone H3B to resistance to 0.1 μM MTX, the expression of human tPA is increased 10-fold.

EXAMPLE 4

Construction of Adjacent Linked Vector

This example contemplates the construction of a transformation vector in which the stop codon of tPA is ligated directed to the start codon of DHFR. This involves deleting the tPA 3' and DHFR 5' untranslated regions from pLDSG constructed in Example 2. This example is based on the use of DNA oligonucleotides to prime DNA synthesis from M13 phage templates (Wallace et al., "Science" 209:1396 [1980]; Zoller et al., Methods in Enzymology Volume 100:468-509). See FIG. 4.

pLDSG is digested with Bam HI and 4.5 kb fragment isolated by gel electrophoresis. This region contains most of the non-pBR/322 regions of pLDSG. Phage M13 mp8 is digested with BamHI. The linearized phage then is ligated to the 4.5 kb fragment of pLDSG and M13 construct used to transform a bacterial host (JM103). Plaques are screened by the Benton-Davis "Science" 196 [1980] procedure using $^{32}$P-labelled probe hybridizing to the tPA gene. Positively hybridizing clones are grown and replicative form DNA prepared. Correct orientation of the tPA gene can be determined in accord with known techniques using restriction endonuclease digestion (BamHI, EcoRI and PvuII).

Figure 4:
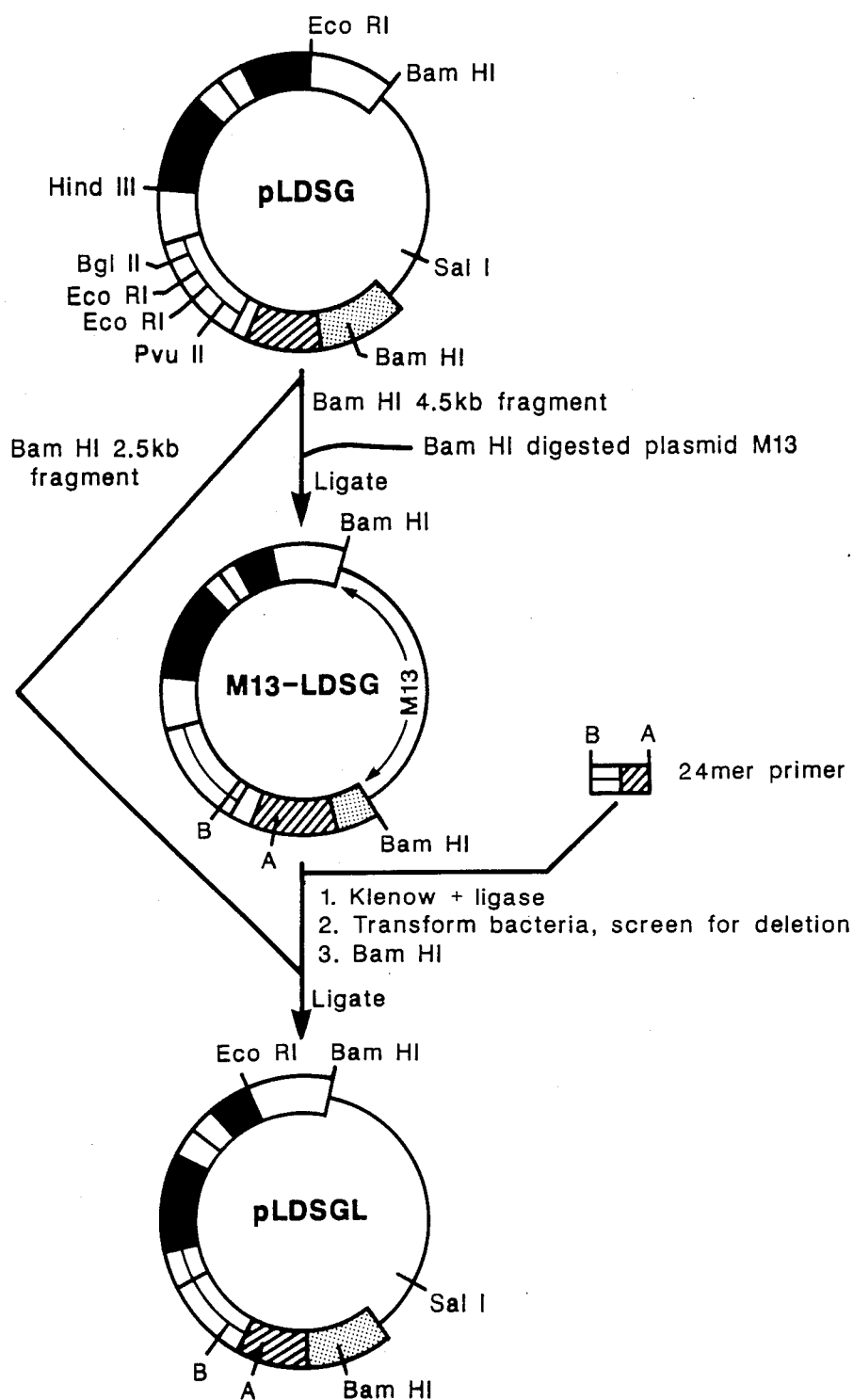
FIG. 4 is a schematic procedure for preparing a linked vector.

Phage DNA is isolated from a plaque demonstrating correct orientation. This single stranded DNA then can be used with a synthetic primer which "bridges" the region of the phage which is to be deleted. The function of the primer is to hybridize to the DNA that is 5' and 3' of the deletion region, thereby looping the undesirable DNA out of position and preventing it from acting as a template in the subsequent primer extension step. In FIG. 4, the 5' and 3' termini of the primer and the corresponding sites in M13-LDSG are designed B and A, respectively.

The primer is prepared by chemical synthesis and consists of 5' -last 9 translated nucleotides of the tPA gene-TAA-ATG-the following 9 translated nucleotides at the amino terminus of DHFR-3'.

The phage DNA and primer are mixed and primer extended by T4 DNA ligase and the Klenow fragment of DNA polymerase I as generally taught in the Wallace et al., and Zoller et al., publications, supra. The product is used to transform JM103. Replicative form phage DNA from plaques which hybridize to $^{32}$P-labelled primer and which are confirmed by Sanger (Sanger et al, Proc. Natl. Acad. Sci. 74 pp. 5463-5467 (1977)) dideoxynucleotide sequencing to have deleted the undesired region are digested with BamHI and the tPA gene-containing fragment isolated by gel electrophoresis. This fragment is isolated from the gel and ligated to the pLDSG 2.5 kb BamHI fragment obtained in the BamHI digestion disclosed above. The ligation products are used to transform E. coli HB101, tetracycline resistant clones identified, plasmid DNA prepared and characterized. A plamid having the correct orientation of the 2.5 and 4.5 kb fragments is identified as pLDSGL.

This plasmid may be used as a linked vector in Example 3 in place of pLDSG and pAdD26SVp(A)3.

EXAMPLE 5

Cotransformation with PBR-deleted Vectors pLDSG is digested with BamHl and the 4.5 kb fragment isolated as shown in FIG. 4. Substantially all of the pBR322 region is discarded with the 2.5 kb fragment from the BamHl digestion. pAdD26SVp(A)3 is digested in the same fashion. The tPA and DHFR gene-containing fragments are used to transform CHO cells as shown in Example 3 for pLDSG and pAdD26SVp(A)3.

EXAMPLE 6

Vector containing Adenovirus Tripartite leader and VA Genes

Figure 5:
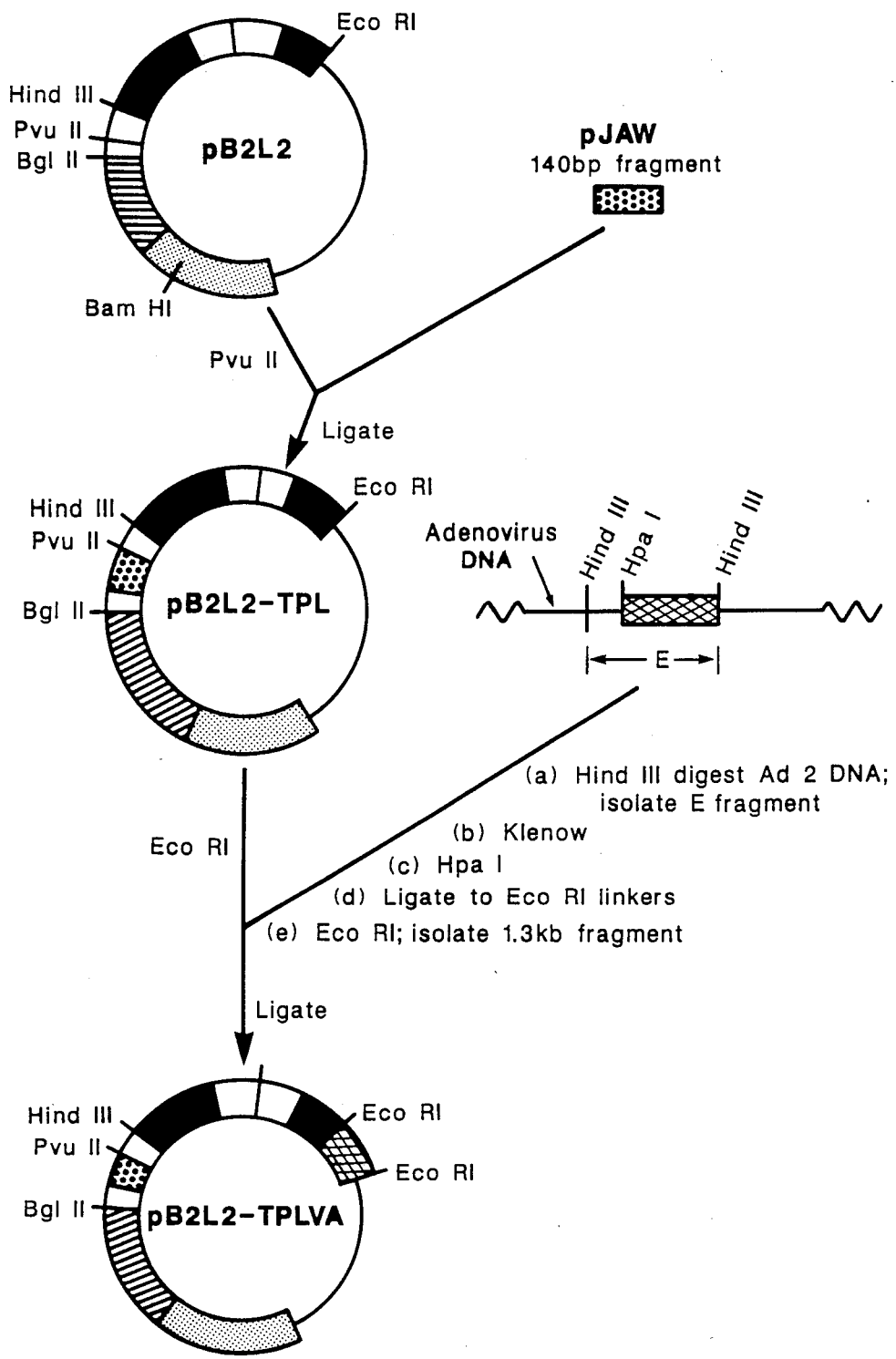
FIG. 5 is a schematic method for making a cotransformation vector containing a translation activator.

The method of this Example is illustrated in FIG. 5. In order to construct a vector containing the adenovirus tripartite leader, one starts with pB2L2 and cleaves it with PvuII to create a linear molecule. Then, pJAW 43 (Zain et al. 1979, Cell 16 851) is digested with Xho 1, treated with Klenow, digested with PvuII, and the 140 base pair fragment is isolated by electrophoresis on an acrylamide gel (6% in Tris borate buffer; Maniatis et al. [1982]supra). The 140 bp fragment then is ligated to the PvuII digested pB2L2. The ligation product is used to transform E. coli to tetracycline resistance and colonies are screened using the Grunstein-Hogness procedure using a $^{32}P$ labeled probe hybridizing to the 140 base pair fragment. DNA is prepared from positively hybridizing colonies to test whether the PvuII site reconstructed is 5' or 3' of the inserted 140 base pair DNA specific to the 2nd and 3rd adenovirus late leaders. In the correct orientation of the PvuII site will be on the 5' side of the 140 base pair insert. This plasmid is designated pB2L2-TPL.

In order to introduce the adenovirus virus associated (VA) gene into the pB2L2-TPL, adenovirus type 2 DNA first is digested with HindIII. The E fragment is isolated after gel electrophoresis in accord with known procedures. This fragment contains the VA genes. This fragment is treated with Klenow, digested with HpaI, ligated to EcoRl linkers (Collaborative), digested with EcoRl, and the 1.3 kb band isolated from an agarose gel. This fragment is ligated into the EcoRl site of pB2L2-TPL (which had previously been digested with EcoRl). After transformation of E. coli HB101 and selection for tetracycline resistance, colonies are screened by filter hybridization to a DNA probe specific to the VA genes. DNA is prepared from positively hybridizing clones and characterized by restriction endonuclease digestion. The product plasmid is designated pB2L2-TPLVA. It is used to advantage in place of pB2L2 in Example 2 to generate modified pLDSG, which in turn is used with pAdD26SVp(A)3 in the Example 3 process.

EXAMPLE 7

Construction of Vector Containing an Immunoglobulin Enhancer e vector pSer has been described (Gillies, et al. "Cell" 33:717-728 [1983]). It is a derivative of pSV2GPT in which the SV40 enhancer is deleted (PvuII to Sph 1, base pairs 64 to 270) (see Mulligan et al., "Science" 209:1422-1427 [1980]). This DNA encodes resistance to mycophenolic acid when cells are grown in the presence of xanthine and hypoxanthine. A 1 kb fragment containing an immunoglobulin enhancer derived from the mouse immunoglobulin constant region gene has been inserted into the EcoRl site of pSer to derive pSerx2/3.

Figure 6A:
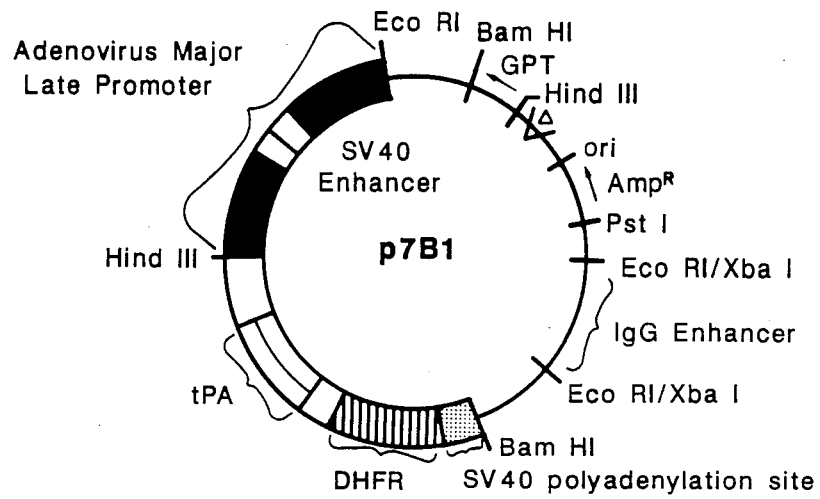
FIG. 6a is a schematic of a transformation vector containing a eucaryotic enhancer.

This vector has a single BamHl site. It is digested with BamHl, treated with alkaline phosphatase and ligated to a fragment of pLDSG which is prepared by BamHl digestion and isolation of the large (4.5 kb) DNA fragment as shown in Example 4. Ligated DNA is used to transform E. coli HB101 which are selected for ampicillin resistance, and colonies are screened by the Grunstein-Hogness procedure for the presence of the tPA gene by hybridization to a $^{32}P$ labeled tPA probe. This probe may be prepared by digestion of J205 with HindIII and SalI and labeling the DNA with T4 DNA polymerase in the presence of a $^{32}P$-alpha-dCTP and cold dTTP, dATP, and dGTP. Positively hybridizing clones are grown and plasmid DNA harvested. FIG. 6a illustrates this vector (p7Bl). This DNA may be introduced into myeloma cells J558L as described by Gillies et al., supra which is a modification of the Sandri-Goldin procedure of protoplast fusion ("Mol. Cell. Bio."1:743-752 (1981)). 36 hours after protoplast fusion, cells are grown in media containing 5 mg/ml mycophenolic acid, 250 ug/ml xanthine and 15 mg/ml hypoxanthine to select for cells that have incorporated the plasmid DNA. One particular clone isolated in this manner expressed tPA at a level of 0.05 mU/cell/day. Another suitable parental cell line would be ATCC CRL1580 or another non-secreting myeloma cell line.

EXAMPLE 8

Construction of Transcriptionally Activated Vector

The trans-acting transcriptional activator ElA is used in cotransformation with a vector containing an adenovirus early region 2 promoter. This promoter, unlike the adenovirus major late promoter, is activated by ElA protein product.

pCVSVL is disclosed by Kaufman et al., "Mol. Cell Biol."2(11):1304-1319 (1982). pCVSVL is digested with Bal 1, treated with Klenow, ligated to XhoI linkers (Collaborative), Xhol digested, EcoRl digested, and the 4.2 kb fragment isolated by gel electrophoresis.

Adenovirus 2 DNA is EcoRl digested and the EcoRl F fragment (map units 70.7–75.9) is recovered. The F fragment was Xhol digested and the E2 promoter subfragment isolated by gel electrophoresis. This subfragment has terminal EcoRl and Xhol cohesive ends and conveniently is ligated to the terminal EcoRl and Xhol gends of the 4.2 kb fragment of pCVSVL obtained as described above. The resulting plasmid is used to transform bacteria. A clone which hybridized to a labelled E2 probe is recovered as pE2-7. pE2-7 is a DHFR cDNA gene which utilizes the adenovirus early region 2 promoter. The construction of pE2-7 was provided by Drs. R. Kingston and P. Sharp.

pE2-7 is partially digested with Pstl treated with Klenow, ligated to BglII linkers and BglII digested. This allows the convenient insertion of the tPA gene from pJ205 (FIG. 3b) into pE2-7.

Figure 6B:
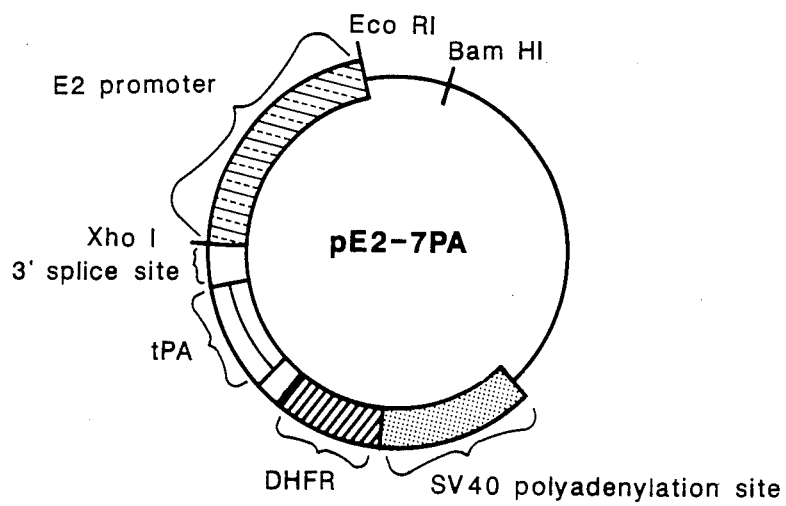
FIG. 6b is a schematic of a transformation vector containing a region susceptible to a trans-acting transcriptonal activator.

A portion of pJ205 bearing the tPA gene is excised from pJ205 as shown in FIG. 3b and the BamHl cohesive ends ligated to the BglII sticky ends of E2-7, producing plasmid pE2-7PA shown in FIG. 6(b). pE2-7PA is a tPA gene which utilizes the adenovirus early region 2 promoter. The ElA gene and promoter are obtained as the Kpnl fragment (0 to 5.8 map units) of Adenovirus 2.

pE2-7PA, pE2-7, and the ElA gene vector are used in molar ratios of (20:1:4) to transform CHO cells as further disclosed in Example 3. Transformants isolated as such produce 0.008m units/cell/day of tPA activity. Transformants obtained by omitting the ElA gene (pE2-7PA with pE2-7 in 20:1 ratio) express only 0.0003 mU/cell/day.

EXAMPLE 9

Alterations in Cell Morphology Related to Elevated tPA Expression

Growth and selection under conditions to optimize for tPA synthesis results in cells with altered morphology which are not capable of attaching to tissue culture dishes. The pool of 300 transformants grown in a media without nucleosides (as described in Example 3, Table 3) which produce low levels of tPA (0.01 mU/cell/day) have a flat morphology characteristic of CHO cells. Upon selection as described in Table 3 for growth in MTX up to 0.05 uM, levels of tPA increase to 0.6 mU/cell/day, and changes in cell morphology become apparent. These alterations are even more apparent in clones producing greater than 1.2 mU/cell/day (for example, clones 9, 12, and 20). These cells do not adhere to the tissue culture dish and thus it is difficult to select for higher levels of tPA expression. This has been overcome by adding aprotinin (Sigma) (0.5% to 5% V/V) to the culture media or by utilizing fetal calf serum which is free of plasminogen. The result of these treatments is to alleviate the toxicity imposed upon cells which are producing high levels of tPA. Plasminogen-free serum can be obtained by passing serum over a column of lysine-Sepharose 4B (Pharmacia) as described (Deutsch & Mertz, *Science* (1970), p. 1095).

I claim:

1. In a method for transforming eukaryotic cells to incorporate a desired product gene by the technique of cotransfecting with unlinked vectors, one of which contains said product gene, the improvement comprising: cotransfecting the cells with
   (a) a first vector comprising an enhancer, a first promoter, and a product gene under the transcriptional control of the first promoter, said first vector not containing a selection gene under the control of the first promoter; and,
   (b) a second unlinked vector comprising a selection gene under the transcriptional control of a second promoter dependant on the enhancer, the second vector not containing the enhancer.

2. A method of claim 1 which further comprises selecting the cotransfected cells so produced which are capable of expressing both the product and selection genes and separating the cells so selected from other cells.

3. Transformed cells produced by the method of claim 2 or progeny thereof.

4. A method for producing a protein product which comprises the steps of culturing a transformed cell of claim 3 in a suitable culture medium and under suitable conditions permitting the expression of the product gene, and recovering the protein product from the medium and the cells.

5. A method of claim 1, wherein each vector also contains a polyadenylation site downstream of the product and selection genes, respectively.

6. Transformed cells produced by the method of claim 5 or progeny thereof.

7. A method for producing a protein product which comprises the steps of culturing a transformed cell of claim 6 in a suitable culture medium and under suitable conditions permitting the expression of the product gene, and recovering the protein product from the medium and the cells.

8. A method of claim 1, wherein the product gene encodes a human tissue plasminogen activator.

9. Transformed cells produced by the method of claim 8 or progeny thereof.

10. A method for producing a human tissue plasminogen activator which comprises the steps of culturing a transformed cell of claim 9 in a suitable culture medium and under suitable conditions permitting the expression of the product gene encoding the human tissue plasminogen activator, and recovering the human tissue plasminogen activator from the medium and the cells.

11. Transformed cells produced by the method of claim 1 or progeny thereof.

12. A method for producing a protein product which comprises the steps of culturing a transformed cell of claim 11 in a suitable culture medium and under suitable conditions permitting the expression of the product gene, and recovering the protein product from the medium and the cells.

* * * * *